United States Patent
Baskin-Bey et al.

(10) Patent No.: US 11,980,626 B2
(45) Date of Patent: May 14, 2024

(54) COMPOSITIONS FOR TREATMENT OF BREAST AND PROSTATE CANCER

(71) Applicant: Kembi Therapeutics Pty Ltd, Carlton (AU)

(72) Inventors: Edwina Baskin-Bey, Los Angeles, CA (US); Joel Eisner, Chapel Hill, NC (US); Elizabeth Woodson, Fuquay-Varina, NC (US)

(73) Assignee: Kembi Therapeutics Pty Ltd, Carlton (AU)

( * ) Notice: Subject to any disclaimer, the term of this patent is extended or adjusted under 35 U.S.C. 154(b) by 140 days.

(21) Appl. No.: 16/894,732

(22) Filed: Jun. 5, 2020

(65) Prior Publication Data

US 2021/0154209 A1    May 27, 2021

Related U.S. Application Data

(63) Continuation of application No. PCT/US2018/064229, filed on Dec. 6, 2018.

(60) Provisional application No. 62/595,918, filed on Dec. 7, 2017.

(51) Int. Cl.
| | |
|---|---|
| *A61K 31/573* | (2006.01) |
| *A61K 31/4192* | (2006.01) |
| *A61K 31/635* | (2006.01) |
| *A61P 35/00* | (2006.01) |
| *C07K 16/28* | (2006.01) |
| *A61K 39/00* | (2006.01) |

(52) U.S. Cl.
CPC ........ *A61K 31/573* (2013.01); *A61K 31/4192* (2013.01); *A61K 31/635* (2013.01); *A61P 35/00* (2018.01); *C07K 16/2803* (2013.01); *A61K 2039/545* (2013.01); *C07K 2317/565* (2013.01)

(58) Field of Classification Search
CPC .... A61K 31/573; A61K 31/4192; A61P 35/00
See application file for complete search history.

(56) References Cited

U.S. PATENT DOCUMENTS

2017/0143694 A1    5/2017    Hoekstra et al.

FOREIGN PATENT DOCUMENTS

JP    2015-212268 A    11/2015

OTHER PUBLICATIONS

International Search Report and Written Opinion mailed Feb. 21, 2019 in connection with PCT/US2018/064229.
Lorente et al., Tumour responses following a steroid switch from prednisone to dexamethasone in castration-resistant prostate cancer patients progressing on abiraterone. Br J Cancer. 2014;111(12):2248-2253. doi:10.1038/bjc.2014.531.
Stein et al., Androgen synthesis inhibitors in the treatment of castration-resistant prostate cancer. Asian J Androl. 2014;16(3):387-400. doi:10.4103/1008-682X.129133.
Extended European Search Report for EP Application No. 18886652.9 mailed Aug. 17, 2021.
International Preliminary Report on Patentability for PCT/US2018/064229 mailed.
Bardia et al., Phase 1 study of seviteronel, a selective CYP17 lyase and androgen receptor inhibitor, in women with estrogen receptor-positive or triple-negative breast cancer. Breast Cancer Res Treat. Aug. 2018; 171(1):111-120. doi: 10.1007/s10549-018-4813-z. Epub May 9, 2018. PMID: 29744674; PMCID: PMC6226357.
Mijatovic et al., Cardiotonic steroids on the road to anti-cancer therapy. Biochim Biophys Acta. Sep. 2007;1776(1):32-57. doi: 10.1016/j.bbcan.2007.06.002. Epub Jul. 4, 2007. PMID: 17706876.
Peer et al., A population pharmacokinetic analysis of the oral CYP17 lyase and androgen receptor inhibitor seviteronel in patients with advanced/metastatic castration-resistant prostate cancer or breast cancer. Cancer Chemother Pharmacol. Oct. 2019;84(4):759-770. doi: 10.1007/s00280-019-03908-0. Epub Jul. 31, 2019. PMID: 31367790; PMCID: PMC8132106.
Yennurajalingam et al., Reduction of cancer-related fatigue with dexamethasone: a double-blind, randomized, placebo-controlled trial in patients with advanced cancer. J Clin Oncol. Sep. 1, 2013;31(25):3076-82. doi: 10.1200/JCO.2012.44.4661. Epub Jul. 29, 2013. PMID: 23897970.
San Juan et al., Targeting phenotypic plasticity prevents metastasis and the development of chemotherapy-resistant disease. medRxiv. Mar. 21, 2022; doi: 10.1101/2022.03.21.22269988. Preprint Author Manuscript. 39 pages.
Petrunak et al., Structural and Functional Evaluation of Clinically Relevant Inhibitors of Steroidogenic Cytochrome P450 17A1. Drug Metab Dispos. Jun. 2017;45(6):635-645. doi: 10.1124/dmd.117.075317. Epub Apr. 3, 2017.

*Primary Examiner* — Alicia L Otton
(74) *Attorney, Agent, or Firm* — Wolf, Greenfield & Sacks, P.C.

(57) ABSTRACT

The instant invention describes pharmaceutical compositions and dosing regimens comprising seviteronel and/or dexamethasone, and methods of treating diseases, disorders or symptoms thereof.

24 Claims, 19 Drawing Sheets

| Subject Disposition & Reason for Study Drug Discontinuation | No Dex[1] N=23 (%) | PLUS Dex[2] N=13 (%) | NEW subjects on DEX[3] N=17 (%) |
|---|---|---|---|
| Median Duration of Study drug in days (range) | 57.0 (15, 223) | 65.0 (54, 176) | 57.0 (22, 155) |
| Median follow-up time in days (range) | 351.0 (150, 612) | 146.0 (57, 365) | 113.0 (22, 372) |
| Ongoing | 0 (0) | 6 (46) | 7 (41) |
| Discontinued from Study | 23 (100) | 7 (54) | 10 (59) |
| Radiographic Progression | 7 (30) | 3 (23) | 4 (24) |
| Adverse Event | 4 (17) | 1 (8) | 2 (12) |
| Withdrawal by Subject | 7 (30) | 2 (15) | 2 (12) |
| Death | 4 (17) | 1 (8) | 2 (12) |

FIG. 1

| Time to Progression | N | Median in days (95% CI) | |
| --- | --- | --- | --- |
| | | No Dex1 | PLUS Dex2 |
| Radiographic progression | 26 | 71 (52, 113) | 109 (57, NE) |
| PSA progression | 60 | 57 (29, NE) | 58 (29, NE) |

| Category | NO Dex[1] N = 23 (%) | PLUS Dex ≥ 30 days[2] N = 13 (%) | New Subjects on Dex[2] N = 17 (%) |
|---|---|---|---|
| Adverse Event | 23 (100) | 11 (85) | 14 (82) |
| Serious Adverse Event | 6 (26) | 3 (23) | 3 (18) |
| Drug Related AE | 19 (83) | 10 (77) | 13 (77) |
| Serious Drug Related AE | 2 (9) | 0 (0) | 0 (0) |
| AE Leading to Discontinuation | 6 (26) | 1 (8) | 2 (12) |
| AE of Grade ≥ 3 | 11 (48) | 5 (39) | 5 (29) |
| Drug Related AE of Grade ≥ 3 | 8 (35) | 2 (15) | 3 (18) |
| AE Leading to Drug Interruption | 11 (48) | 5 (39) | 5 (29) |
| AE Leading to Drug Reduction | 6 (26) | 2 (15) | 1 (6) |
| AE Leading to Death | 0 (0) | 0 (0) | 0 (0) |

FIG. 10

| Event | Grade 1-2 | | Grade ≥ 3 | | All Grades | |
|---|---|---|---|---|---|---|
| | NO Dex[1] N = 23 (%) | New Subjects on Dex[2] N = 12 (%) | NO Dex[1] N = 23 (%) | New Subjects on Dex[2] N = 12 (%) | NO Dex[1] N = 23 (%) | New Subjects on Dex[2] N = 12 (%) |
| Fatigue | 8 (35) | 0 (0) | 1 (4) | 0 (0) | 9 (39) | 0 (0) |
| Dizziness | 8 (35) | 0 (0) | 0 (0) | 0 (0) | 8 (35) | 0 (0) |
| Nausea | 7 (30) | 0 (0) | 0 (0) | 0 (0) | 7 (30) | 0 (0) |
| Tremor | 6 (26) | 0 (0) | 0 (0) | 0 (0) | 6 (26) | 0 (0) |
| Constipation | 4 (17) | 0 (0) | 0 (0) | 0 (0) | 4 (17) | 0 (0) |
| Anemia | 4 (17) | 0 (0) | 0 (0) | 0 (0) | 4 (17) | 0 (0) |
| Confusional state | 3 (13) | 0 (0) | 1 (4) | 0 (0) | 4 (17) | 0 (0) |
| Vision blurred | 2 (9) | 1 (8) | 0 (0) | 0 (0) | 2 (9) | 1 (8) |

FIG. 11

| AE of Special Interest | NO Dex[1] N = 77 | PLUS Dex[2] N = 16 | Relative Risk (95% CI) |
|---|---|---|---|
| Any special AE | 68 (88) | 11 (69) | |
| Fatigue | 37 (48) | 5 (31) | |
| Nausea | 26 (34) | 6 (38) | 1.1 (0.55, 2.2) |
| Dizziness | 26 (34) | 2 (13) | |
| Tremor | 25 (33) | 2 (13) | |
| Constipation | 17 (22) | 2 (13) | |
| Confusional state | 15 (20) | 3 (19) | |
| Vision blurred | 14 (18) | 3 (19) | 1.031 (0.34, 3.2) |
| Vomiting | 11 (14) | 1 (6) | |
| Memory impairment | 10 (13) | 0 (0) | |
| Headache | 9 (12) | 3 (19) | 1.6 (0.49, 5.3) |
| Cognitive disorder | 6 (8) | 0 (0) | |

FIG. 12

| Category | NO Dex[1] | PLUS Dex ≥ 30 days[2] | New Subjects on Dex[3] |
|---|---|---|---|
| Subject Disposition | N = 32 (%) | N = 19 (%) | N = 19 (%) |
| Median time on trial days (range) | 305.5 (14, 542) | 98.0 (30, 248) | 58.0 (7, 167) |
| Ongoing | 4 (12.5) | 12 (63) | 12 (63) |
| Discontinued from Study | N = 28 (%) | N = 7 (%) | N = 7 (%) |
| Due to Radiographic progression | 13 (41) | 5 (26) | 3 (15) |
| Due to adverse event | 5 (16) | 1 (5) | 3 (15) |
| Due to Special Interest | 6 (19) | 0 (0) | 0 (0) |
| Due to death | 2 (6) | 0 (0) | 0 (0) |
| Due to Other causes | 2 (6) | 1 (5) | 1 (5) |

N=58
No SEVI plus Dex End of Treatment samples

*N=89 ER+ BC (O'Shaughnessy et al, 2016)

FIG. 21

| Subjects with Any... | NO Dex¹ N = 32 (%) | PLUS DEX ≥ 30 days² N = 19 (%) | New Subjects on Dex³ N = 19 (%) |
|---|---|---|---|
| Adverse Event | 31 (97) | 15 (79) | 13 (68) |
| Serious Adverse Event | 10 (31) | 9 (47) | 7 (37) |
| Drug Related Adverse Event | 23 (72) | 13 (68) | 11 (58) |
| Serious Drug Related Adverse Event | 3 (9) | 3 (16) | 2 (11) |
| Adverse Event Leading to Permanent Discontinuation | 7 (22) | 3 (16) | 5 (26) |
| Adverse Event of Grade ≥3 | 15 (47) | 9 (47) | 7 (37) |
| Drug Related Adverse Event of Grade ≥3 | 8 (25) | 4 (21) | 3 (16) |
| Adverse Event Leading to Dose Interruption | 13 (41) | 8 (42) | 6 (32) |
| Adverse Event Leading to Dose Reduction | 3 (9) | 5 (26) | 3 (16) |
| Adverse Event leading to Death | 1 (3) | 0 (0) | 0 (0) |

FIG. 22

| Event | Grade 1-2 | | Grade ≥3 | | All Grades | |
|---|---|---|---|---|---|---|
| | NO Dex¹ N = 31 (%) | New Subjects on Dex² N = 13 (%) | NO Dex¹ N = 31 (%) | New Subjects on Dex² N = 13 (%) | NO Dex¹ N = 31 (%) | New Subjects on Dex² N = 13 (%) |
| Nausea | 12 (39) | 1 (8) | 1 (3) | 0 (0) | 13 (42) | 1 (8) |
| Fatigue | 10 (32) | 1 (8) | 2 (6) | 0 (0) | 12 (39) | 1 (8) |
| Vomiting | 10 (10) | 0 (0) | 0 (0) | 1 (8) | 10 (10) | 1 (8) |
| Dizziness | 4 (13) | 1 (8) | 0 (0) | 0 (0) | 4 (13) | 1 (8) |
| Headache | 3 (10) | 1 (8) | 1 (3) | 0 (0) | 4 (13) | 1 (8) |
| Vision Blurred | 3 (10) | 3 (23) | 0 (0) | 0 (0) | 3 (10) | 3 (23) |
| Decreased Appetite | 2 (6) | 0 (0) | 0 (0) | 0 (0) | 2 (6) | 0 (0) |
| Constipation | 1 (3) | 3 (23) | 0 (0) | 0 (0) | 1 (3) | 3 (23) |

FIG. 23

| AE of Special Interest | NO Dex[1] N = 95 (%) | NEW Dex[2] N = 20 (%) | Relative Risk (95% CI) |
|---|---|---|---|
| Any Special AE | 75 (79) | 9 (45) | 0.57 (0.34, 0.94) |
| Fatigue | 42 (44) | 4 (20) | 0.45 (0.18, 1.1) |
| Nausea | 37 (39) | 3 (15) | 0.39 (0.13, 1.1) |
| Constipation | 20 (21) | 4 (20) | 0.95 (0.36, 2.5) |
| Dizziness | 17 (18) | 3 (15) | 0.84 (0.27, 2.6) |
| Tremor | 9 (10) | 2 (10) | 1.1 (0.032, 1.6) |
| Vomiting | 20 (22) | 1 (5) | 0.24 (0.025, 1.2) |
| Vision Blurred | 15 (16) | 3 (15) | 0.89 (0.29, 2.8) |
| Headache | 15 (16) | 2 (10) | 0.63 (0.16, 2.6) |
| Memory Impairment | 8 (8) | 1 (5) | 0.59 (0.079, 4.5) |
| Confusional State | 7 (7) | 3 (15) | 2.04 (0.58, 7.2) |
| Cognitive Disorder | 9 (10) | 0 (0) | N/A |

COMPOSITIONS FOR TREATMENT OF BREAST AND PROSTATE CANCER

CROSS-REFERENCE TO RELATED APPLICATIONS

This application is a continuation of PCT Application No. PCT/US2018/064229, filed Dec. 6, 2018, which claims priority to U.S. Provisional Application No. 62/595,918, filed Dec. 7, 2017, which is incorporated herein by reference in its entirety.

BACKGROUND

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the anti-fungal agent, commonly used to treat prostate cancer, ketoconazole contains a 1-imidazole group that binds to the heme iron present in the active site of the target enzyme CYP17 (17-α-hydroxylase, 17,20-lyase) and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as CYP2C9, CYP2C19 and CYP3A4 by the commonly used prostate anticancer agent ketoconazole. It is believed that this off-target inhibition is caused primarily by the indiscriminate binding of the currently utilized 1-imidazole to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders, and symptoms thereof.

BRIEF SUMMARY OF THE INVENTION

The invention is directed towards compounds (e.g., any of those delineated herein), and methods of treating diseases, disorders, or symptoms thereof. The methods can comprise the compounds herein.

In one aspect, the invention provides a pharmaceutical composition comprising: a) seviteronel, or salt thereof; b) dexamethasone, or salt thereof; and c) a pharmaceutically acceptable carrier. In another aspect, the amount of seviteronel in the composition is in a range of about 150 mg-750 mg. In another aspect, the amount of seviteronel in the composition is in a range of about 400 mg-650 mg. In another aspect, the amount of seviteronel in the composition is 600 mg. In another aspect, the amount of seviteronel in the composition is 450 mg. In another aspect, the amount of dexamethasone in the composition is in a range of about 0.25 mg-1000 mg. In another aspect, the amount of dexamethasone in the composition is in a range of about 0.40 mg-0.60 mg. In another aspect, the amount of dexamethasone in the composition is 0.5 mg. In another aspect, the amount of seviteronel in the composition is in a range of about 150 mg-750 mg, and the amount of dexamethasone in the composition is in a range of about 0.25 mg-1000 mg. In another aspect, the amount of seviteronel in the composition is in a range of about 150 mg-750 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is in a range of about 400 mg-650 mg, and the amount of dexamethasone in the composition is in a range of about 0.25 mg-1000 mg. In another aspect, the amount of seviteronel in the composition is in a range of about 400 mg-650 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is in a range of about 400 mg-650 mg, and the amount of dexamethasone in the composition is 0.5 mg. In another aspect, the amount of seviteronel in the composition is 600 mg, and the amount of dexamethasone in the composition is in a range of about 0.25 mg-1000 mg. In another aspect, the amount of seviteronel in the composition is 600 mg, and the amount of dexamethasone in the composition is in a range of about 0.40 mg-0.60 mg. In another aspect, the amount of seviteronel in the composition is 600 mg, and the amount of dexamethasone in the composition is 0.5 mg. In another aspect, the amount of seviteronel in the composition is 450 mg, and the amount of dexamethasone in the composition is in a range of about 0.25 mg-1000 mg. In another aspect, the amount of seviteronel in the composition is 450 mg, and the amount of dexamethasone in the composition is in a range of about 0.40 mg-0.60 mg. In another aspect, the amount of seviteronel in the composition is 450 mg, and the amount of dexamethasone in the composition is 0.5 mg.

In one aspect, the invention provides a dosing regimen comprising seviteronel, or salt thereof; and dexamethasone, or salt thereof. In another aspect, the amount of seviteronel is in a range of about 150 mg-750 mg. In another aspect, the amount of seviteronel is in a range of about 400 mg-650 mg. In another aspect, the amount of seviteronel is 600 mg. In another aspect, the amount of seviteronel is 450 mg. In another aspect, the amount of dexamethasone is in a range of about 0.25 mg-1000 mg. In another aspect, the amount of dexamethasone is in a range of about 0.40 mg-0.60 mg. In another aspect, the amount of dexamethasone is 0.5 mg. In another aspect, the amount of seviteronel in is in a range of about 150 mg-750 mg, and the amount of dexamethasone is in a range of about 0.25 mg-1000 mg. In another aspect, the amount of seviteronel is in a range of about 150 mg-750 mg, and the amount of dexamethasone is in a range of about 0.40 mg-0.60 mg. In another aspect, the amount of seviteronel is in a range of about 400 mg-650 mg, and the amount of dexamethasone is 0.5 mg. In another aspect, the amount of seviteronel is in a range of about 400 mg-650 mg, and the amount of dexamethasone is in a range of about 0.25 mg-1000 mg. In another aspect, the amount of seviteronel is in a range of about 400 mg-650 mg, and the amount of dexamethasone is in a range of about 0.40 mg-0.60 mg. In another aspect, the amount of seviteronel is in a range of about 400 mg-650 mg, and the amount of dexamethasone is 0.5 mg. In another aspect, the amount of seviteronel is in a range of about 400 mg-650 mg, and the amount of dexamethasone is 0.5 mg. In another aspect, the amount of seviteronel is 600 mg, and the amount of dexamethasone is in a range of about 0.25 mg-1000 mg. In another aspect, the amount of seviteronel is 600 mg, and the amount of dexamethasone is in a range of about 0.40 mg-0.60 mg. In another aspect, the amount of seviteronel is 600 mg, and the amount of dexamethasone is 0.5 mg. In another aspect, the amount of seviteronel is 450 mg, and the amount of dexamethasone is in a range of about 0.25 mg-1000 mg. In another aspect, the amount of seviteronel is 450 mg, and the amount of dexamethasone is in a range of about 0.40 mg-0.60 mg. In another aspect, the amount of seviteronel is 450 mg, and the amount of dexamethasone is 0.5 mg. In another aspect, seviteronel and dexamethasone are administered concurrently. In another aspect, seviteronel and dexamethasone are administered sequentially.

In one aspect, the invention provides a method of treating a subject suffering from or susceptible to a disorder or disease delineated herein, comprising administering to the subject an effective amount of a compound or pharmaceutical composition described herein.

The methods herein include those wherein the disease or disorder is prostate cancer, breast cancer, endometriosis, uterine fibroids, inflammatory bowel disease, psoriasis, systemic fungal infection, onychomycosis, or cardiovascular disease.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which:

FIG. 1. depicts prostate cancer study results for: 1) patients treated with seviteronel and were not treated with dexamethasone at any time during the study (referred to as "NO Dex" in FIG. 1) 2) patients treated with seviteronel and ≥30 days of dexamethasone (referred to as "PLUS Dex" in FIG. 1); and 3) patients treated with seviteronel and dexamethasone within 3 days of Cycle 1 Day 1 study (referred to as "NEW subjects on DEX" in FIG. 1).

FIG. 6. depicts the median time to progression (radiographic progression and PSA progression) for double failure patients treated with: 1) seviteronel and were not treated with dexamethasone at any time during the study (referred to as "NO Dex" in FIG. 6); and 2) seviteronel and ≥30 days of dexamethasone (referred to as "PLUS Dex" in FIG. 6).

FIG. 9. depicts the treatment emergent adverse events (TEAEs) for double failure patients: 1) treated with seviteronel and were not treated with dexamethasone at any time during the study (referred to as "NO Dex" in FIG. 9); 2) treated with seviteronel and ≥30 days of dexamethasone (referred to as "PLUS Dex" in FIG. 9); and 3) treated with seviteronel and dexamethasone within 3 days of Cycle 1 Day 1 study (referred to as "New subjects on Dex" in FIG. 9).

FIG. 10. depicts the adverse event grade level breakdown for double failure patients: 1) treated with seviteronel and were not treated with dexamethasone at any time during the study (referred to as "NO Dex" in FIG. 10); and 2) treated with seviteronel and dexamethasone within 3 days of Cycle 1 Day 1 study (referred to as "New subjects on Dex" in FIG. 10).

FIG. 11. depicts the improved relative risk for patients treated with seviteronel and dexamethasone within 3 days of Cycle 1 Day 1 study (referred to as "New subjects on Dex" in FIG. 11) vs. patients treated with seviteronel and were not treated with dexamethasone at any time during the study (referred to as "NO Dex" in FIG. 11).

FIG. 12. depicts breast cancer study results for: 1) patients treated with seviteronel and were not treated with dexamethasone e at any time during the study (referred to as "NO Dex" in FIG. 12); 2) patients treated with seviteronel and ≥30 days of dexamethasone (referred to as "PLUS Dex" in FIG. 12); and 3) patients, treated with seviteronel and dexamethasone within 3 days of Cycle 1 Day 1 study (referred to as "New subjects on Dex" in FIG. 12).

FIG. 21. depicts treatment emergent adverse events (TE-AEs) for female breast cancer patients: 1) treated with seviteronel and were not treated with dexamethasone at any time during the study (referred to as "NO Dex" in FIG. 21); 2) treated with seviteronel and ≥30 days of dexamethasone (referred to as "PLUS Dex" in FIG. 21); and 3) treated with seviteronel and dexamethasone within 3 days of Cycle 1 Day 1 study (referred to as "New subjects on Dex" in FIG. 21).

FIG. 22. depicts the adverse event grade level breakdown for female breast cancer patients: 1) treated with seviteronel and were not treated with dexamethasone at any time during the study (referred to as "NO Dex" in FIG. 22); and 2) treated with seviteronel and dexamethasone within 3 days of Cycle 1 Day 1 study (referred to as "New subjects on Dex" in FIG. 22).

FIG. 23. depicts the improved relative risk for breast cancer patients treated with seviteronel and dexamethasone within 3 days of Cycle 1 Day 1 study (referred to as "NEW Dex" in FIG. 23) vs. patients treated with seviteronel and were not treated with dexamethasone at any time during the study (referred to as "NO Dex" in FIG. 23).

DETAILED DESCRIPTION

Definitions

Figure 2:
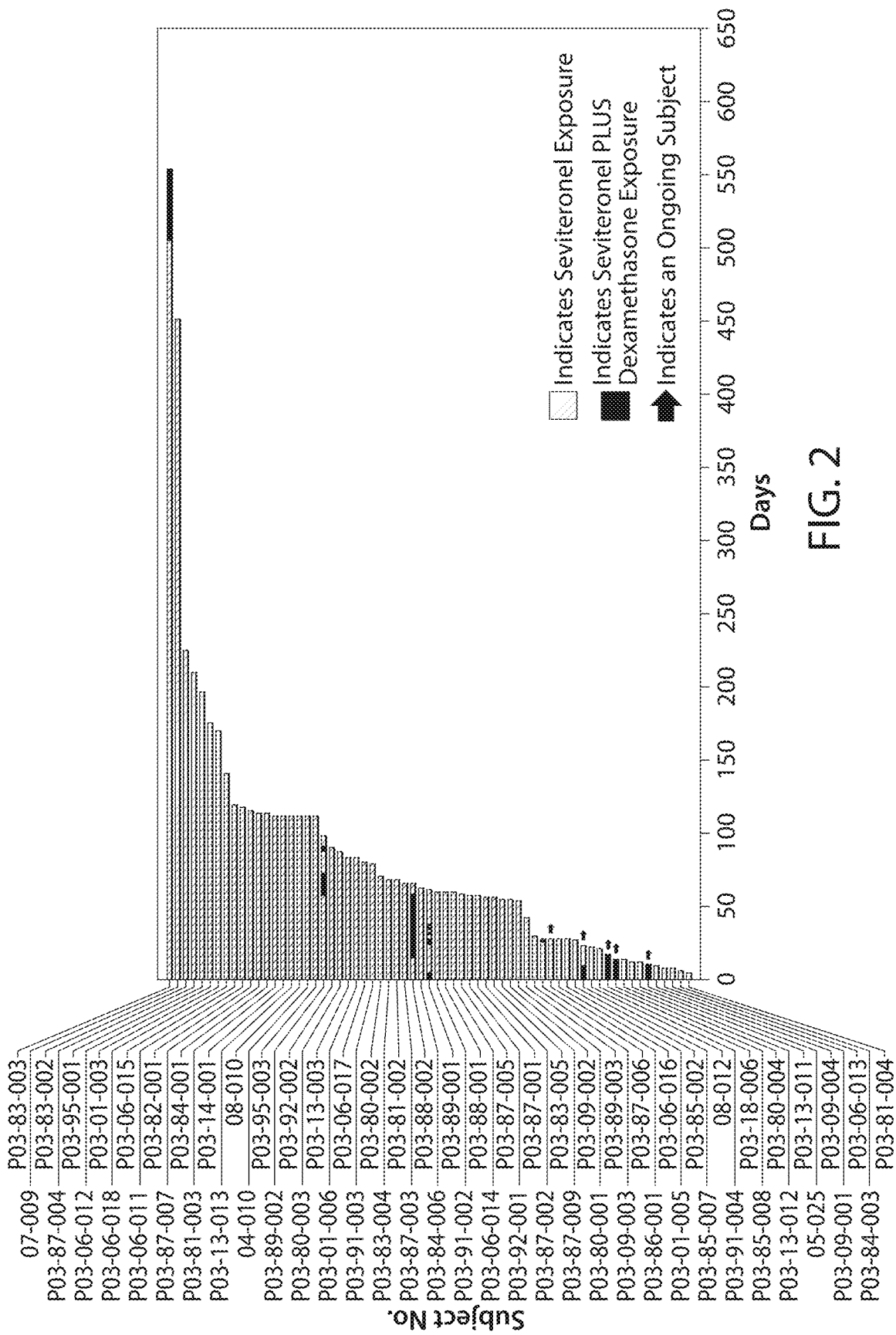
FIG. 2. depicts prostate cancer study results as a Swim Plot for patients who previously failed treatment with enzalutamide or abiraterone (i.e., Single Failure) prior to seviteronel or seviteronel and dexamethasone dosing.

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes art amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "adverse event" or "AE" refers to any untoward medical occurrence in a subject or clinical investigation subject administered a pharmaceutical product, and which does not necessarily have to have a causal relationship with this treatment. An adverse event (AE) can therefore be any unfavorable and unintended sign (including an abnormal laboratory finding, for example), symptom, or disease temporally associated with the use of a medicinal product, whether considered related to the medicinal product.

The term "adverse drug reaction" or "ADR" refers to all noxious and unintended responses to a medicinal product related to any dose. The phrase "responses to a medicinal product" means that a causal relationship between a medicinal product and an adverse event is at least a reasonable possibility, i.e. the relationship cannot be ruled out.

The term "unexpected adverse drug reaction" refers to an AE where the nature or severity of which is not consistent with the applicable product information (e.g., Investigational Brochure, study protocol or Informed Consent Form (ICF)).

The term "serious adverse event" or "SAE" refers to any untoward medical occurrence that at any dose: a) results in death; b) is life-threatening (an event in which the subject was at risk of death at the time of the event; it does not refer to an event which hypothetically might have caused death if it were more severe); c) requires inpatient hospitalization or prolongation of existing hospitalization; d) results in persistent or significant disability/incapacity; e) is a congenital anomaly or birth defect; f) other important medical events that may not be immediately life-threatening or result in death or hospitalization but may jeopardize the subject or may require intervention to prevent one of the other outcomes listed above. Examples of such events are intensive treatment in an emergency room for allergic bronchospasm; blood dyscrasias or convulsions that do not result in hospitalization; or development of drug dependency or drug abuse. The term "severe" is often used to describe the intensity (severity) of an event; the event itself may be of relatively minor medical significance (such as a severe headache). This is not the same as "serious," which is based on subject/event outcome or action criteria usually associated with events that pose a threat to a subject's life or functioning.

An AE may be classified as being "unrelated" to the study drug if the event has no temporal relationship to study drug administration (too early or late or study drug not taken), or there is a reasonable causal relationship between the AE and another drug, concurrent disease, or circumstance.

An AE may be classified as being "related" to the study drug if the event has a temporal relationship to drug administration which makes a causal relationship improbable, and in which other drugs, chemicals or underlying disease provide plausible explanations.

An AE may be classified as being "possibly related" to the study drug if the event follows a reasonable temporal sequence from administration of the study drug and the event follows a known response pattern to the study drug BUT the event could have been produced by an intercurrent medical condition which, based on the pathophysiology of the condition, and the pharmacology of the study drug, would be unlikely related to the use of the study drug or the event could be the effect of a concomitant medication.

An AE may be classified as being "probably related" to the study drug if the event follows a reasonable temporal sequence from administration of the study drug and the event follows a known response pattern to the study drug AND the event cannot have been reasonably explained by an intercurrent medical condition or the event cannot be the effect of a concomitant medication.

An AE may be classified as being "definitely related" to the study drug if the event follows a reasonable temporal sequence from administration of the study drug, the event follows a known response pattern to the study drug and based on the known pharmacology of the study drug, the event is clearly related to the effect of the study drug.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm Sci*, 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" (or plus and minus) configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond, Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

The term "haloalkoxy" refers to an —O-alkyl radical that is substituted by one or more halo substituents. Examples of haloalkoxy groups include trifluoromethoxy, and 2,2,2-trifluoroethoxy.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl,1,3-dioxolanyl, tetrahydrofuranyl, tetrahydrothienyl, thienyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, haloalkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N''-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, 2$^{nd}$ Edition, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include. diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In another embodiment, the invention provides a method of treating breast cancer or prostate cancer in a subject, comprising administering to the subject in need thereof any pharmaceutical composition or dosing regimen described herein. In another embodiment, the invention provides a method of treating breast cancer or prostate cancer in a subject, comprising administering to the subject in need thereof any pharmaceutical composition or dosing regimen described herein, such that the number of and/or severity of adverse events are less than when said pharmaceutical composition or dosing regimen does not contain dexamethasone. In another embodiment, the invention provides a method of treating breast cancer or prostate cancer in a subject, comprising administering to the subject in need thereof any pharmaceutical composition or dosing regimen described herein, such that the time to progressive disease (e.g., radiographic progression, PSA progression, tumor growth, and the like) is increased relative to the absence of the administration of said pharmaceutical composition or dosing regimen. In another embodiment, the invention provides a method of treating breast cancer or prostate cancer in a subject, comprising administering to the subject in need thereof any pharmaceutical composition or dosing regimen described herein, such that the ACTH drive is decreased, adrenal androgens are decreased, and/or up-stream steroids are decreased relative to a pharmaceutical composition or dosing regimen devoid of dexamethasone.

In another embodiment, the invention provides a method of treating a subject suffering from or susceptible to breast cancer or prostate cancer, comprising administering to said subject any pharmaceutical composition or dosing regimen described herein. In another embodiment, the invention provides a method of treating a subject suffering from or susceptible to breast cancer or prostate cancer, comprising administering to said subject any pharmaceutical composition or dosing regimen described herein, such that the number of and/or severity of adverse events are less than when said pharmaceutical composition or dosing regimen does not contain dexamethasone. In another embodiment, the invention provides a method of treating a subject suffering from or susceptible to breast cancer or prostate cancer, comprising administering to said subject any pharmaceutical composition or dosing regimen described herein, such that the time to progressive disease (e.g., radiographic progression, PSA progression, tumor growth, and the like) is increased relative to the absence of the administration of said pharmaceutical composition or dosing regimen. In another embodiment, the invention provides a method of treating a subject suffering from or susceptible to breast cancer or prostate cancer, comprising administering to said subject any pharmaceutical composition or dosing regimen described herein, such that the ACTH drive is decreased, adrenal androgens are decreased, and/or up-stream steroids are decreased relative to said pharmaceutical composition or dosing regimen devoid of dexamethasone.

In certain embodiments, the invention provides a method of treating a disease, disorder or symptom thereof, wherein the disorder is prostate cancer, breast cancer, androgen-dependent cancers, estrogen-dependent cancers, inflammatory bowel disease, psoriasis, systemic fungal infection, onychomycosis, adrenal hyperplasia, prostatic hypertrophy, virilism, hirsutism, male pattern alopecia, precocious puberty, endometriosis, uterus myoma, uterine cancer, uterine fibroids, mastopathy, polycystic ovary syndrome, infertility, acne, functional ovarian hyperandrogenism, hyperandrogenism with chronic anovulation, hyperandrogenemia, premature adrenarche, adrenal or androgen excess.

In certain embodiments, the invention provides a method of treating a disease, disorder or symptom thereof, wherein the disorder is prostate cancer, breast cancer, androgen-dependent cancers, estrogen-dependent cancers, adrenal hyperplasia, prostatic hypertrophy, virilism, hirsutism, male pattern alopecia, precocious puberty, endometriosis, uterus myoma, uterine cancer, uterine fibroids, mastopathy, polycystic ovary syndrome, infertility, acne, functional ovarian hyperandrogenism, hyperandrogenism with chronic anovulation, hyperandrogenemia, premature adrenarche, adrenal or androgen excess.

In certain embodiments, the subject is a mammal, preferably a primate or human.

In another embodiment, the invention provides a method as described above, wherein the effective amount of a compound or composition described herein.

In another embodiment, the invention provides a method as described above, wherein any compound or composition described herein is administered intravenously, intramuscularly, subcutaneously, intracerebroventricularly, orally or topically.

As used herein, "a CYP 17 related disorder" is a physiological or pathological state that is dependent on the activity of CYP17. Non-limiting examples of CYP17 related disorders include prostate cancer, breast cancer, adrenal hyperplasia, prostatic hypertrophy, virilism, hirsutism, male pattern alopecia, precocious puberty, endometriosis, uterus myoma, uterine cancer, mastopathy, polycystic ovary syndrome, infertility, acne, functional ovarian hyperandrogenism, hyperandrogenism with chronic anovulation, hyperandrogenemia, premature adrenarche, adrenal and androgen excess.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Pharmaceutical Compositions

In one aspect, the invention provides a pharmaceutical composition comprising: a) seviteronel, or salt thereof; b) dexamethasone, or salt thereof; and c) a pharmaceutically acceptable carrier. In another aspect, the amount of seviteronel in the composition is in a range of about 150 mg-750 mg. In another aspect, the amount of seviteronel in the composition is in a range of about 400 mg-650 mg. In another aspect, the amount of seviteronel in the composition is 600 mg. In another aspect, the amount of seviteronel in the composition is 450 mg. In another aspect, the amount of dexamethasone in the composition is in a range of about 0.25 mg-1000 mg. In another aspect, the amount of dexamethasone in the composition is in a range of about 0.40 mg-0.60 mg. In another aspect, the amount of dexamethasone in the composition is 0.5 mg. In another aspect, the amount of seviteronel in the composition is in a range of about 150 mg-750 mg, and the amount of dexamethasone in the composition is in a range of about 0.25 mg-1000 mg. In another aspect, the amount of seviteronel in the composition is in a range of about 150 mg-750 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is in a range of about 400 mg-650 mg, and the amount of dexamethasone the composition is in a range of about 0.25 mg-1000 mg. In another aspect, the amount of seviteronel in the composition is in a range of about 400 mg-650 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is in a range of about 400 mg-650 mg, and the amount of dexamethasone in the composition is 0.5 mg. In another aspect, the amount of seviteronel in the composition is 600 mg, and the amount of dexamethasone in the composition is in a range of about 0.25 mg-1000 mg. In another aspect, the amount of seviteronel in the composition is 600 mg, and the amount of dexamethasone in the composition is in a range of about 0.40 mg-0.60 mg. In another aspect, the amount of seviteronel in the composition is 600 mg, and the amount of dexamethasone in the composition is 0.5 mg. In another aspect, the amount of seviteronel in the composition is 450 mg, and the amount of dexamethasone in the composition is in a range of about 0.25 mg-1000 mg. In another aspect, the amount of seviteronel in the composition is 450 mg, and the amount of dexamethasone in the composition is in a range of about 0.40 mg-0.60 mg. In another aspect, the amount of seviteronel in the composition is 450 mg, and the amount of dexamethasone in the composition is 0.5 mg.

In one aspect, the invention provides a dosing regimen comprising seviteronel, or salt thereof; and dexamethasone, or salt thereof. In another aspect, the amount of seviteronel is in a range of about 150 mg-750 mg. In another aspect, the amount of seviteronel is in a range of about 400 mg-650 mg. In another aspect, the amount of seviteronel is 600 mg. In another aspect, the amount of seviteronel is 450 mg. In another aspect, the amount of dexamethasone is in a range of about 0.25 mg-1000 mg. In another aspect, the amount of dexamethasone is in a range of about 0.40 mg-0.60 mg. In another aspect, the amount of dexamethasone is 0.5 mg. In another aspect, the amount of seviteronel in is in a range of about 150 mg-750 mg, and the amount of dexamethasone is in a range of about 0.25 mg-1000 mg. In another aspect, the amount of seviteronel is in a range of about 150 mg-750 mg, and the amount. of dexamethasone is in a range of about 0.40 mg-0.60 mg. In another aspect, the amount of seviteronel is in a range of about 400 mg-650 mg, and the amount of dexamethasone is 0.5 mg. In another aspect, the amount of seviteronel is in a range of about 400 mg-650 mg, and the amount of dexamethasone is in a range of about 0.25 mg-1000 mg. In another aspect, the amount of seviteronel is in a range of about 400 mg-650 mg, and the amount of dexamethasone is in a range of about 0.40 mg-0.60 mg. In another aspect, the amount of seviteronel is in a range of about 400 mg-650 mg, and the amount of dexamethasone is 0.5 mg. In another aspect, the. amount of seviteronel is in a range of about 400 mg-650 mg, and the amount of dexamethasone is 0.5 mg. In another aspect, the amount of seviteronel is 600 mg, and the amount of dexamethasone is in a range of about 0.25 mg-1000 mg. In another aspect, the amount of seviteronel is 600 mg, and the amount of dexamethasone is in a range of about 0.40 mg-0.60 mg. In another aspect, the amount of seviteronel is 600 mg, and the amount of dexamethasone is 0.5 mg. In another aspect, the amount of seviteronel is 450 mg, and the amount of dexamethasone is in a range of about 0.25 mg-1000 mg. In another aspect, the amount of seviteronel is 450 mg, and the amount of dexamethasone is in a range of about 0.40 mg-0.60 mg. In another aspect, the amount of seviteronel is 450 mg, and the amount of dexamethasone is 0.5 mg. In another aspect, seviteronel and dexamethasone are administered concurrently. In another aspect, seviteronel and dexamethasone are administered sequentially.

In one aspect, the invention provides a pharmaceutical composition comprising any compound(s) described herein.

In one aspect, the invention provides a kit comprising an effective amount of any compound(s) described herein, or combinations thereof, in unit dosage form, together with instructions for administering the compound to a subject suffering from or susceptible to prostate cancer, breast cancer, androgen-dependent cancers, estrogen-dependent cancers, inflammatory bowel disease, psoriasis, systemic fungal infection, onychomycosis, adrenal hyperplasia, prostatic hypertrophy, virilism, hirsutism, male pattern alopecia, precocious puberty, endometriosis, uterus myoma, uterine cancer, uterine fibroids, mastopathy, polycystic ovary syndrome, infertility, acne, functional ovarian hyperandrogenism, hyperandrogenism with chronic anovulation, hyperandrogenemia, premature adrenarche, adrenal or androgen excess.

In one aspect, the invention provides a kit comprising an effective amount of any compound(s) described herein, or combinations thereof, in unit dosage form, together with instructions for administering the compound to a subject suffering from or susceptible to prostate cancer, breast cancer, androgen-dependent cancers, estrogen-dependent cancers, adrenal hyperplasia, prostatic hypertrophy, virilism, hirsutism, male pattern alopecia, precocious puberty, endometriosis, uterus myoma, uterine cancer, uterine fibroids, mastopathy, polycystic ovary syndrome, infertility, acne, functional ovarian hyperandrogenism, hyperandrogenism with chronic anovulation, hyperandrogenemia, premature adrenarche, adrenal or androgen excess.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also be used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments, containing conventional suppository bases, such as cocoa butter or other glycerides, For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil.) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro CHMC or BMMC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) can not be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of Seviteronel (aka VT-464 and INO-464: 1-(6,7-Bis(difluoromethoxy)naphthalen-2-yl)-2-methyl-1-(1H-1,2,3-triazol-4-yl)propan-1-ol)

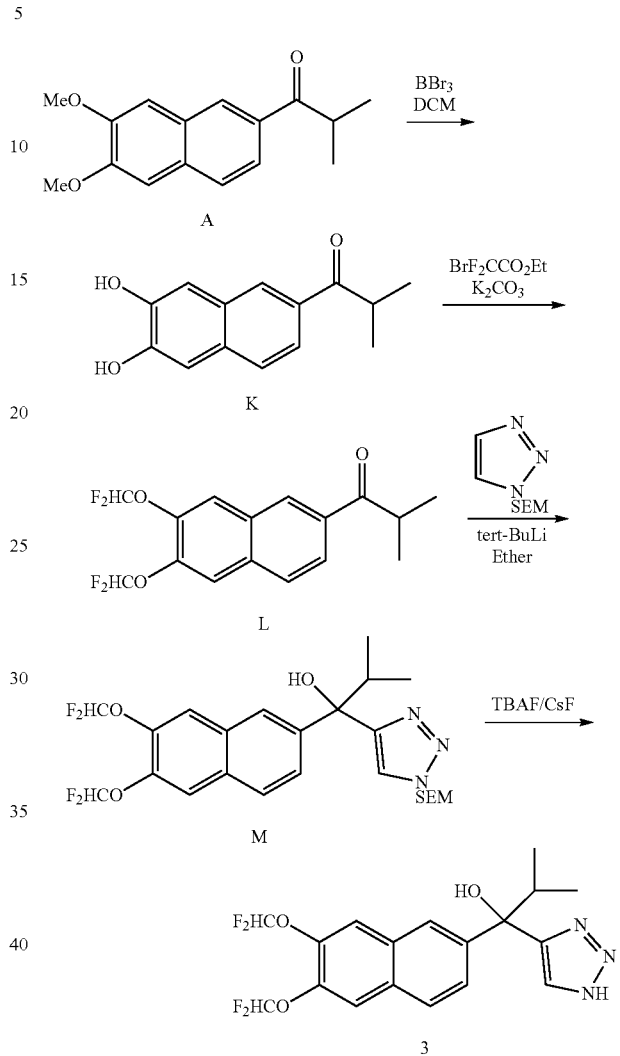

Example 1

1-(6,7-Bis(difluoromethoxy)naphthalen-2-yl)-2-methyl-1-(1H-1,2,3-triazol-4-yl)propan-1-ol(3)

To a stirred solution of A (18 g, 69 mmol) in DCM (180 mL) was added BBr$_3$ (87.2 g, 348 mmol) dropwise at −40° C. After completion of addition, stirring was continued for 1 h at −40° C. and 1 h at RT. The reaction mixture was poured into cold water and aqueous layer was then extracted with DCM (2×200 mL). The combined organic extracts were washed with water (100 mL), brine (100 mL) and dried over anhydrous Na$_2$SO$_4$. After filtration and evaporation of solvent under reduced pressure, the crude material was purified by column chromatography (SiO$_2$, 100-200 mesh) to afford K (9.0 g, 39 mmol, 56%) as a brown solid. $^1$H NMR (200 MHz, CDCl3):δ 8.29 (s, 1H), 7.88 (dd, J=8.8, 1.6 Hz, 1H), 7.68 (d, J=8.6 Hz, 1H), 7.36 (s, 1H), 7.26 (s, 1H), 5.88 (br s, 2H), 3.79-3.63 (m, 1H), 1.27 (d, J=6.8 Hz, 6H).

To a stirred solution of K (5.0 g, 21.7 mmol) in DMF (50 mL) were added ethyl bromo difluoroacetate (17.6 g, 86.6 mmol) and K$_2$CO$_3$ (18 g, 130 mmol) and the mixture was stirred at 110° C. for 48 h. The reaction mixture was poured into cold water and aqueous layer was then extracted with DCM (2×100 mL). Combined organic extracts were washed with water (50 mL), brine (50 mL), and dried over anhydrous Na$_2$SO$_4$. After filtration and evaporation of solvent under reduced pressure, the crude material was purified by column chromatography (SiO$_2$, 100-200 mesh) to afford L (2.3 g, 4.3 mmol, 32%) as a solid. $^1$H NMR (500 MHz, CDCl3): δ☐8.40 (s, 1H), 8.05 (dd, J=8.5, 1.5 Hz, 1H), 7.86 (d, J=9.0 Hz, 1H), 7.79 (s, 1H), 7.68 (s, 1H), 6.67 (t, J$_{F,H}$=73 Hz, 1H), 6.65 (t, J$_{F,H}$=73 Hz, 1H), 3.72-3.65 (m, 1H), 1.27 (d, J=7.0 Hz, 6H).

To a stirred solution of N-SEM-1,2,3-triazole (2.25 g, 11.8 mmol) in dry ether (25 mL) was added t-BuLi (0.69 g, 10.7 mmol) dropwise at −78° C. under inert atmosphere. After stirring for 1 h at −78° C., compound-L (1.5 g, 2.83 mmol) in dry ether (25 mL) was added to reaction mixture and stirring was continued for additional 1 h at −78° C. The reaction mixture was quenched with saturated NH$_4$Cl solution and extracted with ethyl acetate (2×50 mL). Combined organic phases were washed with brine, dried over anhydrous Na$_2$SO$_4$ and concentrated under reduced pressure to afford M (2.0 g) as thick syrup. Crude material was taken up for next step without further purification.

To a stirred solution of M (3.0 g, 5.6 mmol) in THF (30 mL) were added TBAF (1.48 g, 5.67 mmol, 1 M in THF) and CsF (2.58 g, 16.8 mmol) at RT under inert atmosphere. The reaction mixture was stirred at 80° C. for 4 h. The mixture was concentrated in vacuo; the obtained residue was partitioned between water and DCM. The organic phase was separated and the aqueous layer was extracted with DCM (2×25 mL); the combined organic phases were washed with brine, dried over anhydrous Na$_2$SO$_4$, and concentrated under reduced pressure to give crude material. The crude material was purified by column chromatography (SiO$_2$, 100-200 mesh) to afford 3 (2.2 g, 5.5 mmol, 61%) as a white solid. $^1$H NMR (500 MHz, CDCl3): δ☐11.4 (br, 1H), 8.03 (s, 1H), 7.76-7.61 (m, 5H), 6.60 (t, J$_{F,H}$=74 Hz, 2H). 2.88 (br s, 1H), 2.86-2.80 (m, 1H). 0.97 (d, J=7.0 Hz, 3H), 0.80 (d, J=7.0 Hz, 3H). HPLC: 96%. MS (ESI): m/z, 398 [M+H]$^+$.

(−)-Enantiomer of (3)
  Chiral preparative HPLC Specifications
  Column: Chiralpak IC, 250×4.6 mm, 5-micron
  Mobile Phase: A) n-Hexane, B) IPA
  Isocratic: A:B (95:5)
  Flow rate: 1.00 mL/min
  HPLC: 99.5% (13 mg isolated as a white powder).
  Optical rotation [α]$_D$: 54° (c=0.5% in MeOH).

Treatment of Prostate Cancer in Men With Seviteronel
  Males that fulfill the Inclusion Criteria captured in Table 1 were administered seviteronel (600 mg; 4×150 mg tablets) once daily until any of the criteria in Table 2 are met. Table 3 captures the clinical screening data and screening schedule for the various screens for each of the male subjects.

TABLE 1

Inclusion Criteria for Prostate Cancer Treatment Studies

≥18 years of age
Documented histological or cytological evidence of adenocarcinoma of the prostate. Subjects whose pathology reports are no longer available may be enrolled if, in the opinion of the investigator, the subject has a clinical course consistent with prostatic adenocarcinoma TABLE 1-continued Inclusion Criteria for Prostate Cancer Treatment Studies ECOG Performance Status of 0 or 1
Undergone orchiectomy, or have ongoing LHRH analogue therapy prior to receiving first dose of seviteronel or Sevi-D. Subjects on LHRH analogues must remain on these agents for the duration of the study
Castrate levels of testosterone ≤50 ng/dl (or 1.7 nmol/L) and have progressive disease at screening defined as PSA rise determined by a minimum of 2 rising PSA values ≥1 week between each assessment. The PSA value at the Screening visit must be ≥2 ng/mL with or without:
Soft tissue disease progression defined by RECIST 1.1 at Screening or ≤28 days of receiving first dose of seviteronel or Sevi-D. Measurable disease is not required for entry. Lymph nodes ≥1.5 cm (short axis) are considered measurable disease (PCWG3, Scher 2016)
Bone disease progression defined by ≥2 new lesions on bone scan at Screening, or ≤28 days of receiving first dose of seviteronel or Sevi-D
Have received abiraterone and/or enzalutamide. Subject must have received either abiraterone or enzalutamide for ≥12 weeks. Other second generation CYP17 inhibitors/androgen receptor antagonists including but not limited to TAK-700 (orteronel), TOK-001 (galeterone) may have been taken in place of abiraterone and ARN-509 (apalutamide) may have been taken in place of enzalutamide.
WBC ≥ 3,000/µl
ANC ≥ 1,500/µl
Platelet count ≥ 100,000/µl
HGB ≥ 10 g/dl and not transfusion dependent
Total serum bilirubin ≤2.0 × ULN unless the subject has documented Gilbert syndrome;
Aspartate and alanine aminotransferase (AST & ALT) ≤3.0 × ULN or ≤5.0 × ULN if subject has liver metastasis;
Alkaline phosphatase ≤3.0 × ULN or ≤5 × ULN in case of bone metastasis and/or hepatic metastasis
Serum creatinine of ≤2.0 mg/dl
Potassium (K+) ≥ 3.5 mEq/l

TABLE 2

Criteria For Withdrawal From Prostate Cancer Studies

Voluntary withdrawal by the subject
Development of progressive neoplastic disease per RECIST 1.1 or PCWG3 criteria for radiographic progression and who are no longer receiving clinical benefit from study treatment
Development of a medical condition and need for prohibited concomitant treatment that precludes further participation in the study.
An adverse event which in the opinion of the Investigator precludes further participation in the study.
The Investigator removes the subject-from the study in the best interests of the subject.

TABLE 3

Schedule of Procedures and Screening

| Day of Cycle | Screening −28 days to −1 | Cycle 1 Day 1 +/−3 d | Cycle 1 Day 15 +/−3 d | Cycle 2 Day 1 +3 d | ≥Cycle 3 Day 1 +/−3 d | End of Study withing 30 days of last dose |
|---|---|---|---|---|---|---|
| Treatment | | | | | | |
| Obtain informed consent | X | | | | | |
| Seviteronel administration | | Continuous dosing once daily | | | | |
| Dexamethasone | | Continuous dosing once daily | | | | |
| History and Physical | | | | | | |
| Medical History | X | X[1] | | | | |
| Adverse event reporting | | | X | X | X | X |
| Concomitant medication reporting | X | X | X | X | X | X |
| Physical exam | X | X | X | X | X | X |
| ECOG performance Status | X | X | X | X | X | X |
| Height | X | | | | | |
| Weight | X | X | X | X | X | X |
| Vital signs[2] | X | X | X | X | X | X |
| Laboratory and Safety Assessments | | | | | | |
| CBC with differential | X | X[3] | X | X | X | X |
| Comprehensive Metabolic Panel | X | X[3] | X | X | X | X |
| Ca, Mg, Phos, LDH | X | X[3] | X | X | X | X |
| Urinalysis[4] | X | | | | | X |
| ECG | X | | | | | X |
| Serum testosterone | X | | | | | |
| PSA | X | X[3] | X | X | X | X |
| PTT/PT (or INR) | X | X[3] | | As clinically indicated | | |
| Tumor Assessments | | | | | | |
| Imaging for metastatic disease (scintigraphy and CT or MRI) | X[5] | | | | X (Cycle 3, 5, 7 then every 3 cycles) | X[5] |
| Correlative Biomarkers | | | | | | |
| Biopsy to collect tumor tissue[6] | X | | | | | X[7] |
| WBC buffy coat Pharmacogenetics | X | | | | | X |
| Blood sample for CTCs (Univeristy of Wisconsin Versa platform) | X | | | | X (Cycle 3) | X[7] |
| Blood sample for circulating tumor DNA | X | | | X | X (Cycle 3, 4, 5, 6 then every 2 cycles) | X[7] |
| Blood sample for serum androgens using Univ. Wash. assay | X | | | X | | X[7] |

Notes:

[1]Collect full medical history at screening. At C1D1, confirm medical history and update medical history with any new events between signing of informed consent and C1D1

[2]Vital signs include sitting blood pressure, pulse, respiratory rate, and temperature (includes height at screening only)

[3]Does not need to be repeated if already completed within 7 days of C1D1

[4]Urninalysis to include specific gravity, and hemoglobin, glucose, ketones, and protein by microscopic exam

[5]May be performed within 8 weeks of informed consent; extent of disease evaluation should include all appropriate radiographic or scintigraphic procedures to document areas of metastatic disease.

[6]Subjects will have a tumor biopsy performed at baseline if safe and feasible. Subjects who demonstrate evidence of benefit from therapy (defined by ≥50% decline in PSA or PFS >6 months on therapy) will have a tumor biopsy at End of Study if safe and feasible. Biopsies will not be required for subjects without radiographic evidence of disease. One of the buffy coat samples at the time of study entry and tumor samples from study entry and at the time of progression will be sent for DNA sequencing +/− RNA sequencing. Exact sequencing methodology to be determined depending on availability at the time of study opening. Biopsy of a soft tissue lesion is preferable over a bone lesion if safe and feasible.

[7]Every effort should be made to have these performed while still on seviteronel or as soon as possible thereafter. This is to enable accurate assessment of all ongoing pharmacodynamic drug effects when analyzing these samples. These repeat biomarker studies are not required if they have already been drawn in the preceding 14 days as part of another study visit.

Treatment of Prostate Cancer in Men With Seviteronel and Dexamethasone (Sevi-D)

Males that fulfill the Inclusion Criteria captured in Table 1 were administered seviteronel (600 mg; 4×150 mg tablets) and dexamethasone (0.5 mg) once daily until any of the criteria in Table 2 are met. Table 3 captures the clinical screening data and screening schedule for the various screens for each of the male subjects.

Treatment of Breast Cancer in Men and Women With Seviteronel

Subjects that fulfill the Inclusion Criteria captured in Table 4 were administered seviteronel (600 mg for male subjects, 4×150 mg tablets; 450 mg for female subjects, 3×150 mg tablets) once daily until any of the criteria in Table 2 are met. Table 5 captures the clinical screening data and screening schedule for the various screens for each of the male subjects.

TABLE 4

Inclusion Criteria for Breast Cancer Treatment Studies

≥18 years of age
Have documented histological or cytological evidence of invasive cancer of the breast, defined by one of the following:
ER+ breast cancer, defined as positive if ≥1% by IHC and HER2 normal, defined as IHC 0-1+ or IHC 2+ (and FISH < 2), or FISH < 2.0
TNBC, defined as ER−/PgR− if 0% by IHC and HER2 normal, defined TABLE 4-continued Inclusion Criteria for Breast Cancer Treatment Studies as IHC 0-1+ or IHC 2+ (and FISH <2), or FISH <2.0
Subjects with ER+/HER2 normal tumors must have progression of disease following at least 1 prior line of endocrine therapy.
ECOG PS of 0 or 1 for Females, 0, 1, or 2 for Males.
Undergoing or willing to undergo gonadal suppression:
Female subjects with ER+/HER2 normal tumors must be post-menopausal defined by local practice. Ovarian suppression with a LHRH analogue to achieve cessation of regular menses is allowed on study
Male subjects must be undergoing or willing to undergo gonadal suppression whilst on study drug and continue with the LHRH analogue for the duration of the study
WBC ≥ 3,000/µl
ANC ≥ 1,500/µl
Platelet count ≥ 100,000/µl
HGB ≥ 9 g/dl and not transfusion dependent
Total serum bilirubin ≤2.0 × ULN unless the subject has documented Gilbert syndrome;
Aspartate and alanine aminotransferase (AST & ALT) ≤3.0 × ULN or ≤5.0 × ULN if subject has liver metastasis;
Alkaline phosphatase ≤3.0 × ULN or ≤5 × ULN in case of bone metastasis and/or hepatic metastasis
Serum creatinine of ≤2.0 mg/dl
Potassium (K+) ≥ 3.5 mEq/l
Women of child-bearing potential must have a negative serum or urine pregnancy test within 72 hours of receiving first dose of seviteronel or Sevi-D.

TABLE 5

Schedule of Procedures and Screening

| Procedure | Screening (Day −28) | Cycle 1 D1 | Cycle 1 D14 +/−2 Days | C2D1 +2 Days | Subsequent Cycles D1 +/−2 Days | EOT[17] | Every 3 Months |
|---|---|---|---|---|---|---|---|
| Informed Consent | X | | | | | | |
| Medical History | X | X[1] | | | | | |
| Complete Physical Exam | X | | | | | X | |
| Brief Physical Exam[2] | | X | | X | X | | |
| Vital Signs[3] | X | X | X | X | X | X | |
| Weight | X | X | | X | X | X | |
| Height | X | | | | | | |
| ECOG Perfomance Status | X | X | X | X | X | X | |
| ECG | X | | | | | X | |
| CBC[4] | X[5] | X[6] | | X[6] | X[6] | X[6] | |
| Serum Chemistry[7] | X[5] | X[6] | X[6] | X[6] | X[6] | X[6] | |
| Urinalysis[8] | X[5] | | | | | X[5] | |
| Pregnancy test[9] | X[9] | X[9] | | | | | |
| Endocrine Panel[10] | X | X | | X | X | X | |
| Radiographic Response Assessment[11] | X | | | X | X | X | |
| Phase 2 PK Sampling | | X[12] | X | X | X[12] | | |
| Blood for Pharmacogenomics and ctDNA [18] | X | X | X | X | X | X | |
| Tumor collection[13] | X | | | | | | |
| AE reporting[14] | | x————————————————▶ | | | | | |
| Con Med reporting[14] | | x————————————————▶ | | | | | |
| Administration of seviteronel[15] | | | x ———————————————▶ | | | | |

TABLE 5-continued

Schedule of Procedures and Screening

| Procedure | Screening (Day −28) | Cycle 1 | | C2D1 +2 Days | Subsequent Cycles D1 +/−2 Days | EOT[17] | Every 3 Months |
|---|---|---|---|---|---|---|---|
| | | D1 | D14 +/−2 Days | | | | |
| Admistration of oral dexamethanone[16] | | x | | | → | | |
| Survival Follow-up | | | | | | | X[19] |

Notes:
[1]Collect full medical history at screening. At C1D1, confirm medical history and update medical history with any new events between signing of informed consent and C1D1
[2]Physical exams should be brief and targeted on areas known to be abnormal, or driven by clinical findings and/or subject complaints.
[3]Vital signs to include sitting blood pressure, pulse, respiratory rate, and temperature, and should be collected at a single time point.
[4]CBC to include white blood count, hemoglobin, hematocrit white count differential (absolute counts) and platelet count.
[5]Assessment does not need to be repeated at C1D1 if completed within 7 days of C1D1.
[6]Results do not need to be available prior to treatment.
[7]Serum chemistries to include sodium, potassium, chloride, bicarbonate, BUN, creatinine, glucose, AST, ALT, alkaline phosphatase, total bilirubin, total protein, magnesium, calcium, phosphorous.
[8]Urinalysis to include specific gravity, pH, glucose, ketones, bilirubin, hemoglobin and protein via microscopy.
[9]Pregnancy test for women of child-bearing potential must be completed within 72 hours of C1D1.
[10]Endocrine panel is a single morning time point and should be processed and stored per laboratory manual.
[11]Assessment should include CT or MRI of the chest, abdomen, and pelvis and bone scintigraphy at baseline. Screening assessments must be completed within 8 weeks of informed consent. Scans should be repeated at the end of even-numbered cycles (e.g., after cycle 2, 4, 6, 8 etc.) through the first 12 months of treatment and every 3 months thereafter. Scans may be completed +/− 7 days of the planned visit date. Bone scans to be followed in subjects who have bone disease at baseline and as clinically indicated. EOT scans to be performed within 4 weeks of end of treatment and prior to initiation of a new therapy.
[12]PK schedule for subjects at C1D1 is a single morning time point. Samples should be drawn at time points as noted and then every even-numbered cycle beginning with C4D1. Time and date of last dose of seviteronel before PK draws should be recorded. The timing of PK samples for Phase 2 subjects may be changed based on emerging data.
[13]Subjects will have an archival tumor tissue specimen, or recent biopsy specimen submitted for biomarker analyses during screening.
[14]Adverse events and concomitant medications should be reported from the time of signing informed consent until 30 days after last dose of study medication or until the subject begins another regimen. Adverse events that occur before C1D1 should be captured on the Medical History Page.
[15]Subjects will be instructed to take seviteronel each evening with dinner (unless advised by sponsor and/or medical monitor to administer at an alternative time of day).
[16]Subjects will be instructed to take dexamethasone orally each morning starting on C1D1.
[17]EOT visit to occur 30 days (±7 days) after last dose of seviteronel or discontinuation of study activities. Out of window exception. EOT visit should be completed prior to starting new therapy.
[18] Peripheral blood to be collected for pharmacogenomics (Screening only), ctDNA. The timing of collection for pharmacogenomics, ctDNA, may be changed based on emerging data.
[19]Survival information collected every 3 months following, last dose of seviteronel until death or study data cutoff date.

Treatment of Breast Cancer in Men and Women With Seviteronel and Dexamethasone (Sevi-D)

Subjects that fulfill the Inclusion Criteria captured in Table 4 were administered seviteronel (600 mg for male subjects, 4×150 mg tablets; 450 mg for female subjects, 3×150 mg tablets) and dexamethasone (0.5 mg) once daily until any of the criteria in Table 2 are met. Table 5 captures the clinical screening data and screening schedule for the various screens for each of the male subjects.

Medical History

A careful medical history, with attention to the subject's history of disease (e.g., prostate cancer or breast cancer) and prior therapy for said disease, was obtained during Screening and reviewed on the first day of receiving treatment with seviteronel or seviteronel and dexamethasone (Sevi-D). Other pertinent aspects of the subject's medical history were obtained. Previous use of anti-androgens and anti-hormonal medications for treatment of prostate cancer were also recorded.

ECOG Performance Status

Below are the grade levels for ECOG performance status evaluation:

| Grade | ECOG |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities. Up and about more than 50% of waking hours |
| 3 | Capable of only limited selfcare, confined to bed or chair more than 50% of waking hours |
| 4 | Completely disabled. Cannot carry on any selfcare. Totally confined to bed or chair |
| 5 | Dead |

Determination of Extent of Metastatic Disease

All subjects underwent an extent of disease evaluation consisting of bone scintigraphy and CT or magnetic resonance imaging of the abdomen and pelvis at screening unless conducted within 8 weeks of the informed consent date. Subjects who had evaluable and/or measurable metastases at screening underwent repeat evaluations of their extent of disease or as clinically indicated. Imaging modality should remain consistent by lesion throughout study.

Complete Blood Count (CBC)

HGB, HCT, WBC, differential (absolute values preferred) and platelet count were obtained at Initial Screening and at all study visits.

Serum Chemistries

Sodium, potassium, chloride, bicarbonate, BUN, glucose, creatinine, AST, ALT, alkaline phosphatase, lactate dehydrogenase, bilirubin, total protein, albumin, globulin, calcium, magnesium, phosphorous, troponins I and T, and creatine kinase—MB were obtained at Initial Screening and at all study visits.

Urinalysis

Specific gravity, and hemoglobin, glucose, ketones, and protein by microscopic exam via urine sample were measured at screening and at the final visit.

Tumor Biopsy

Subjects had normal tissue (buffy coat of blood) collected and tumor biopsy performed if was deemed safe and feasible (biopsy was not required for subjects without radiographic evidence of disease). The buffy coat and tumor were sent for DNA sequencing +/− RNA expression analysis. Blood samples were also be collected and sent to University of Wisconsin for CTC analysis using their VERSA platform.

Circulating Tumor Cells (CTCs)

Blood samples were collected and sent to Epic Sciences Inc. (San Diego, California) for CTC analysis using their next-generation CTC platform at baseline and at specific time points during the study schedule as outlined in the Tables 3 and 6. Blood samples were also collected and sent to University of Wisconsin for CTC analysis using their VERSA platform.

CTCs (classical, EMT-like, small cell, and apoptotic subtypes) were measured at Initial Screening, on the first day of receiving treatment with seviteronel or seviteronel and dexamethasone, 15 days after receiving the first dose of either seviteronel or seviteronel and dexamethasone (Sevi-D), and every 4 to 8 weeks until time of progression.

Samples were analyzed for CTC numbers (classical, EMT-like, small cell, and apoptotic subtypes), immunofluorescence for AR expression and localization, presence of AR v7 (with N and C terminal expression), immunofluorescence for GR and FISH for ERG/PTEN.

Circulating Tumor DNA (ctDNA)

Variant polymorphisms and mutations in ctDNA were examined in relation to response to seviteronel or seviteronel and dexamethasone. Serial collection of ctDNA was performed for targeted sequencing over time and for correlation with tumor sequencing where available.

Genomic DNA from WBC Buffy Coat

The WBC buffy coat were obtained from the same tube used for ctDNA. Genomic DNA front one buffy coat sample were used in the analysis of the tumor biopsy. The genomic DNA was analyzed for polymorphisms in CYP17 lyase, other CYP enzymes, drug transporters, and other genes that may be linked to efficacy or adverse events with seviteronel or seviteronel and dexamethasone (e.g., DMET chip).

Endocrine Panel

Blood samples were collected for evaluation of steroid hormone changes as a pharmacodynamics indicator of CYP17 inhibition over time e.g., DHEA, DHEA-S, androstenedione, testosterone, cortisol, corticosterone, progesterone, pregnenolone, estradiol, estrone and ACTH).

Safety Analysis

The Safety Analysis Set consists of all subjects who received at least 1 dose of seviteronel. Safety parameters include results of adverse event reporting, physical exam findings, vital signs, safety laboratory determinations, ACTH stimulation tests, ECGs, and Holter monitoring. Adverse events are listed per the most recent MedDRA coding dictionary.0 by system organ class, preferred term and high level terms. All adverse events are classified by type, severity, and causality. In addition to all adverse events, serious adverse events, drug-related adverse events, Grade 3 or higher adverse events, drug-related Grade 3 or higher adverse events, and adverse events leading to discontinuation or death are described. The World Health Organization (WHO) Drug Dictionary is used to classify concomitant medications by therapeutic class and preferred term.

Efficacy Analysis

The Efficacy Analysis Set consists of all subjects who received at least 1 dose of seviteronel and had at least 1 post-dose assessment of PSA; for subjects with evaluable and/or measurable metastases at screening, 1 post-dose assessment of metastatic disease was required. Changes in PSA were compared to baseline by dose; maximal change from baseline and change at Week 12 were also be determined, as was duration of response. Maximum change in soft tissue lesions as seen on CT or MRI of the abdomen and pelvis, as well as changes on bone scintigraphy per the PCWG2 criteria were also compared to baseline, and summarized by dose. In the presence of new bone lesions at the first restaging scan at the end of Cycle 2 which could be bone flare, subsequent scans were compared to that scan as the new baseline scan but if there was progression noted on the next scan at the end of Cycle 4, the progression date was when the first new lesions were noted (Scher H I, Halabi S, Tannock I, Morris M, Sternberg C N, Carducci M A, et al. Design and end points of clinical trials for patients with progressive prostate cancer and castrate levels of testosterone: recommendations of the Prostate Cancer Clinical Trials Working Group. J Clin Oncol 2008; 26(7):1148-1159). Additional details regarding the efficacy analysis will be described in the statistical analysis plan.

Correlative Biomarker Analysis

An exploratory endpoint of the study was to evaluate the predictive accuracy of potential biomarkers for the PSA response and PFS endpoints. Other exploratory objectives include assessment of mechanisms of resistance to seviteronel via biomarker analysis of post-progression tumor tissue. A Cox proportional hazards regression model (for the time to progression endpoint) and a logistic regression model (for the PSA response endpoint) was used to assess the prognostic significance of baseline factors both alone and in combination with other biomarkers (e.g., clinical parameters, LDH, Hb). For each regression model, the c-index will be used to quantify the predictive accuracy of these biomarkers. The models will be stratified by cohort group to bundle the four cohorts into one correlative analysis.

Results

Treatment of Prostate Cancer in Men With Seviteronel Or Seviteronel and Dexamethasone (Sevi-D)

Figure 3:
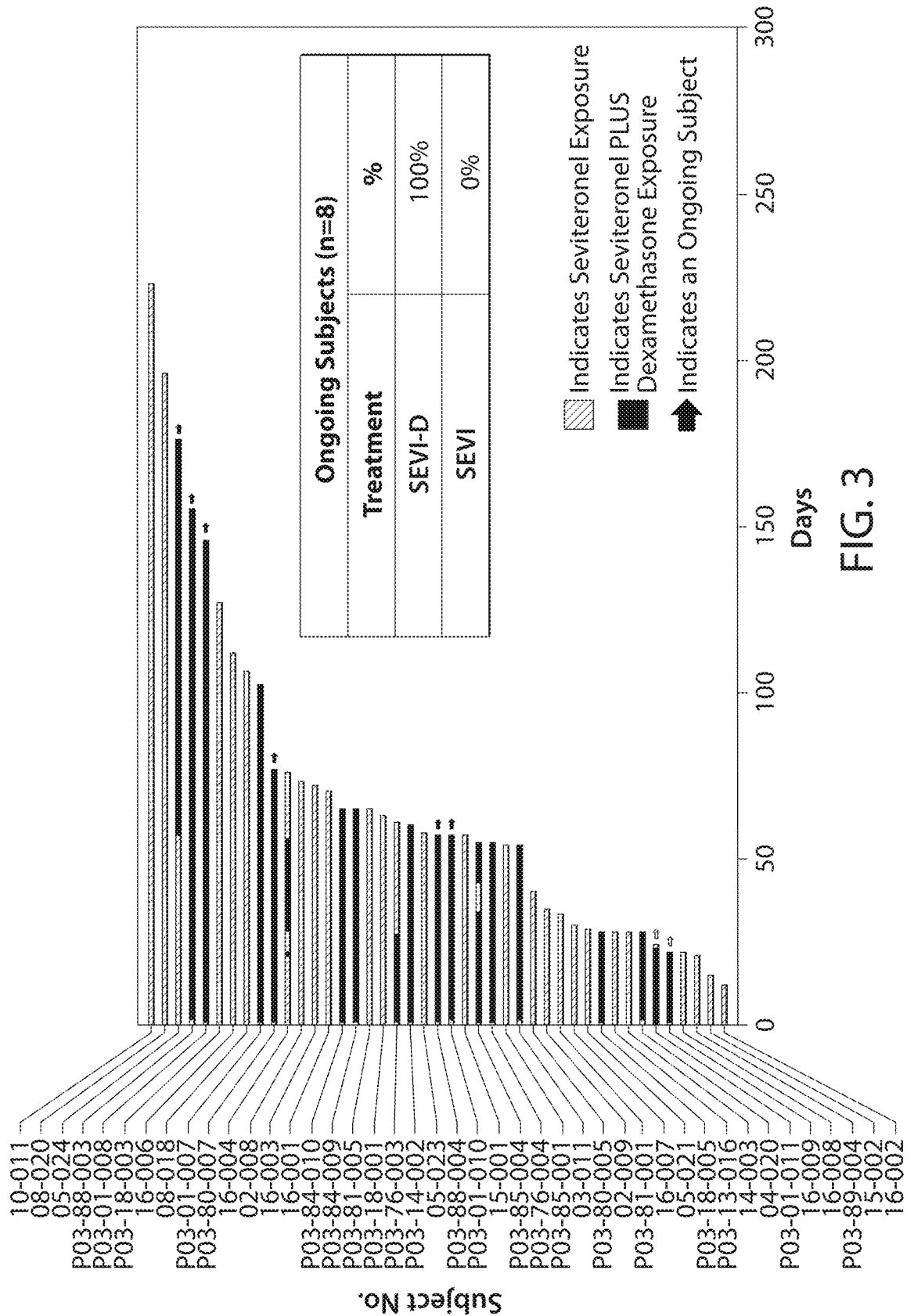
FIG. 3. depicts the Swim Plot for patients who had previously failed enzalutamide and abiraterone (i.e., Double Failure) prior to seviteronel or seviteronel and dexamethasone dosing.
Figure 4:
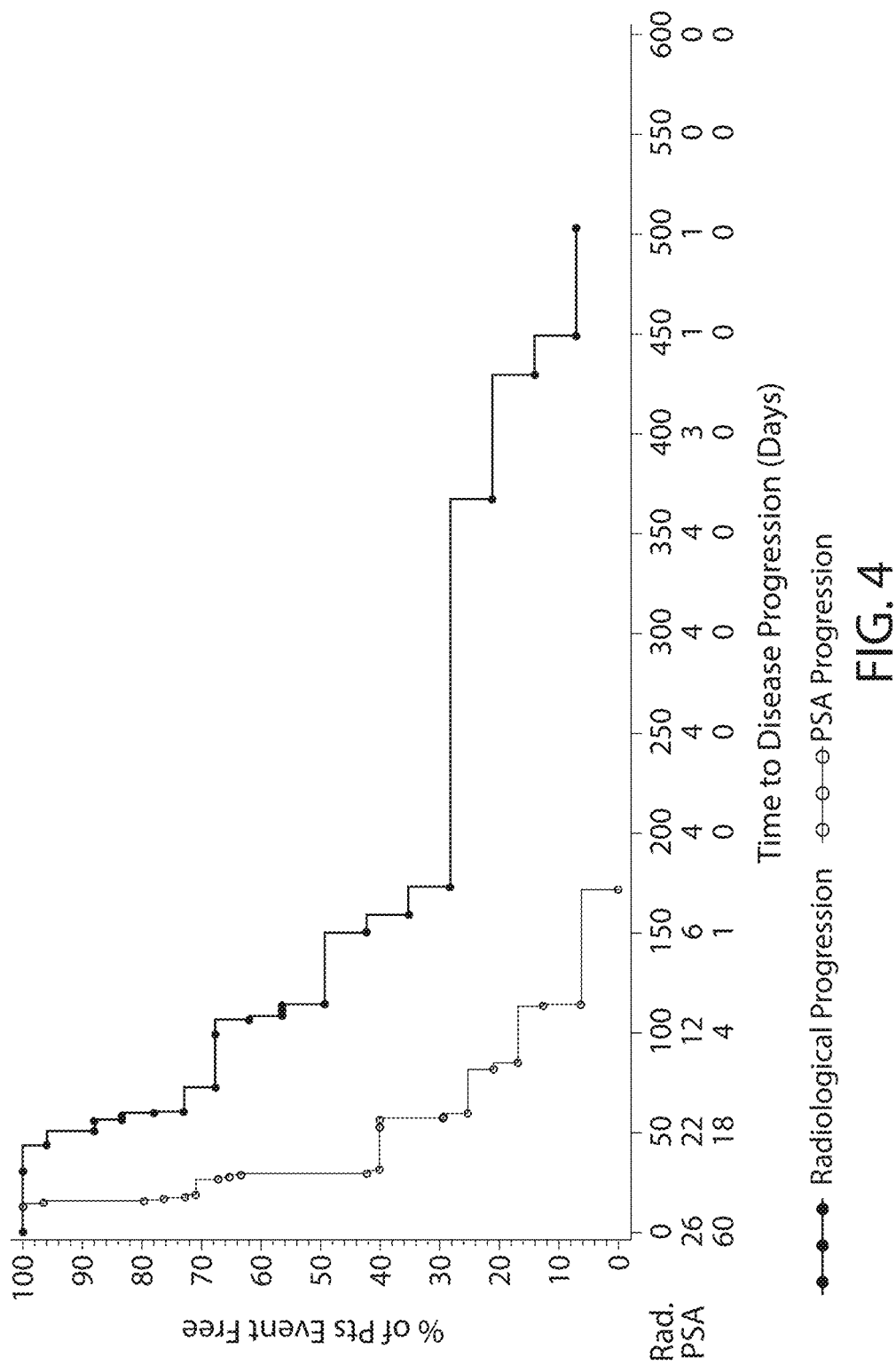
FIG. 4. depicts the Kaplan-Meier estimates (radiographic progression and PSA progression) for single failure patients treated with SEVI (i.e., seviteronel) and SEVI-D (i.e., seviteronel and dexamethasone).
Figure 5:
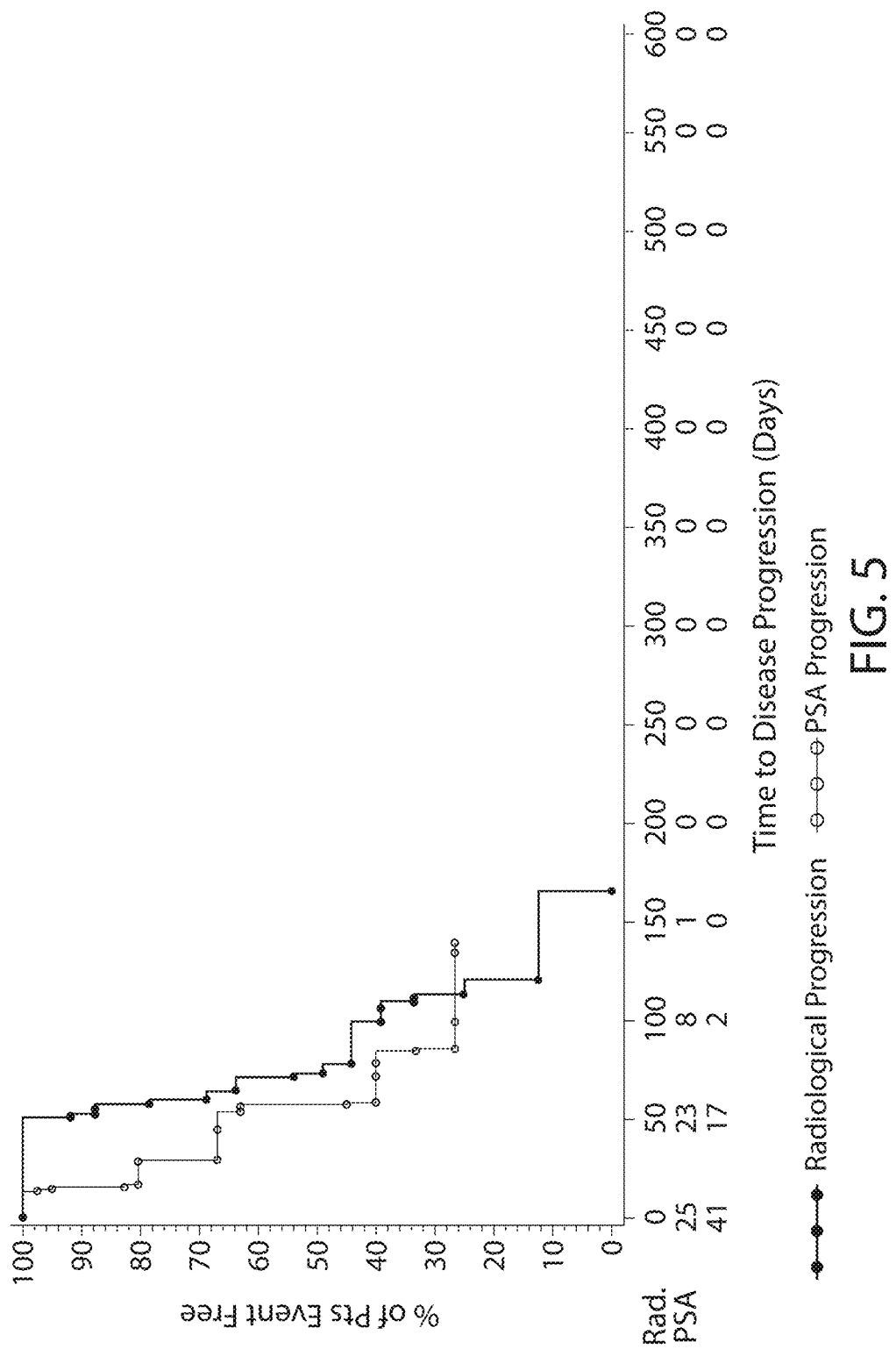
FIG. 5. depicts the Kaplan-Meier estimates (radiographic progression and PSA progression) for double failure patients treated with SEVI (i.e., seviteronel) and SEVI-D (i.e., seviteronel and dexamethasone).

FIG. 1 captures the prostate cancer study results for: 1) patients treated with seviteronel and were not treated with dexamethasone at any time during the study (referred to as "NO Dex" in FIG. 1); 2) patients treated with seviteronel and ≥30 days of dexamethasone (referred to as "PLUS Dex" in FIG. 1); and 3) patients treated with seviteronel and dexamethasone within 3 days of Cycle 1 Day 1 study (referred to as "NEW subjects on DEX" in FIG. 1). FIG. 2 summarizes the prostate cancer study results as a Swim Plot for patients who previously failed treatment with enzalutamide or abiraterone (i.e., Single Failure) prior to seviteronel or seviteronel and dexamethasone dosing, while FIG. 3 illustrates the Swim Plot for patients who had previously failed enzalutamide and abiraterone (i.e., Double Failure) prior to seviteronel or seviteronel and dexamethasone dosing. FIGS. 4 and 5 capture the Kaplan-Meier estimates (radiographic progression and PSA progression)

for single failure and double failure patients, respectively, treated with SEVI (i.e., seviteronel) and SEVI-D (seviteronel and dexamethasone).

FIG. 6 summarizes the median time to progression (radiographic progression and PSA progression) for double failure patients treated with: 1) seviteronel and were not treated with dexamethasone at any time during the study (referred to as "NO Dex" in FIG. 6); and 2) seviteronel and ≥30 days of dexamethasone (referred to as "PLUS Dex" in FIG. 6).

Figure 7:
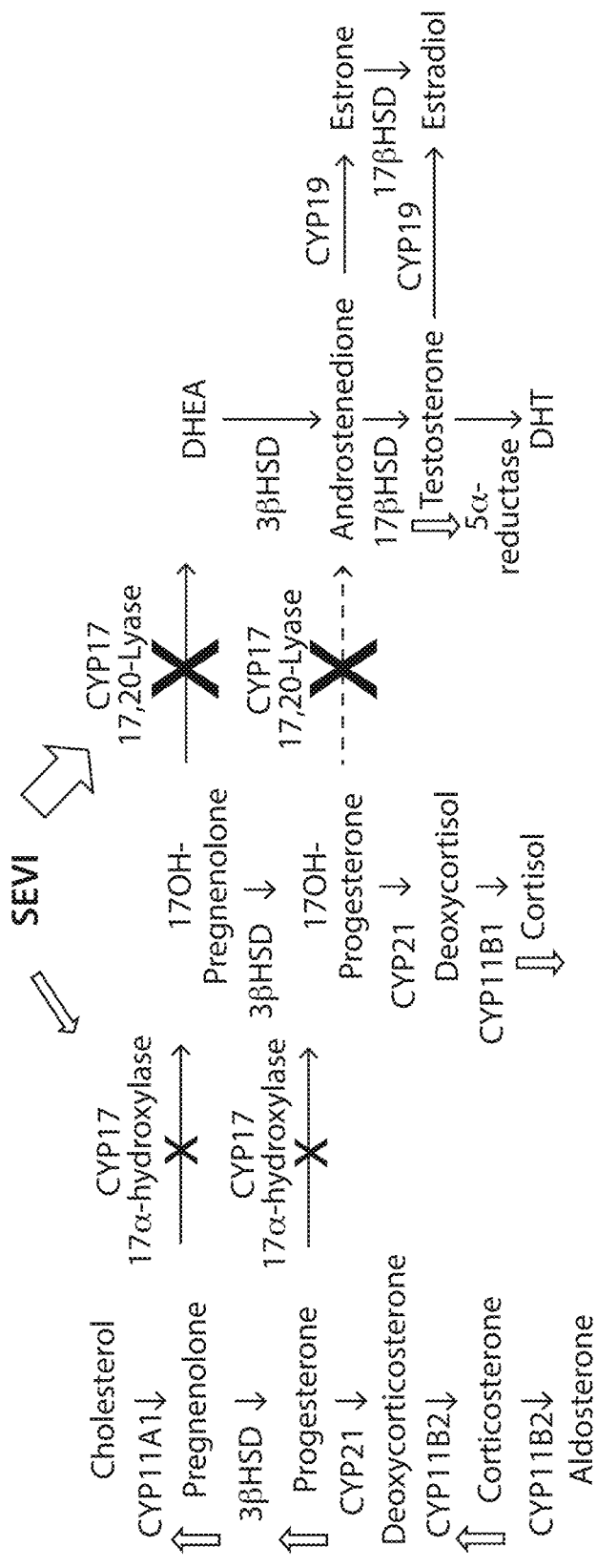
FIG. 7. depicts the endocrine profile for prostate cancer patients treated with SEVI.
Figure 8:
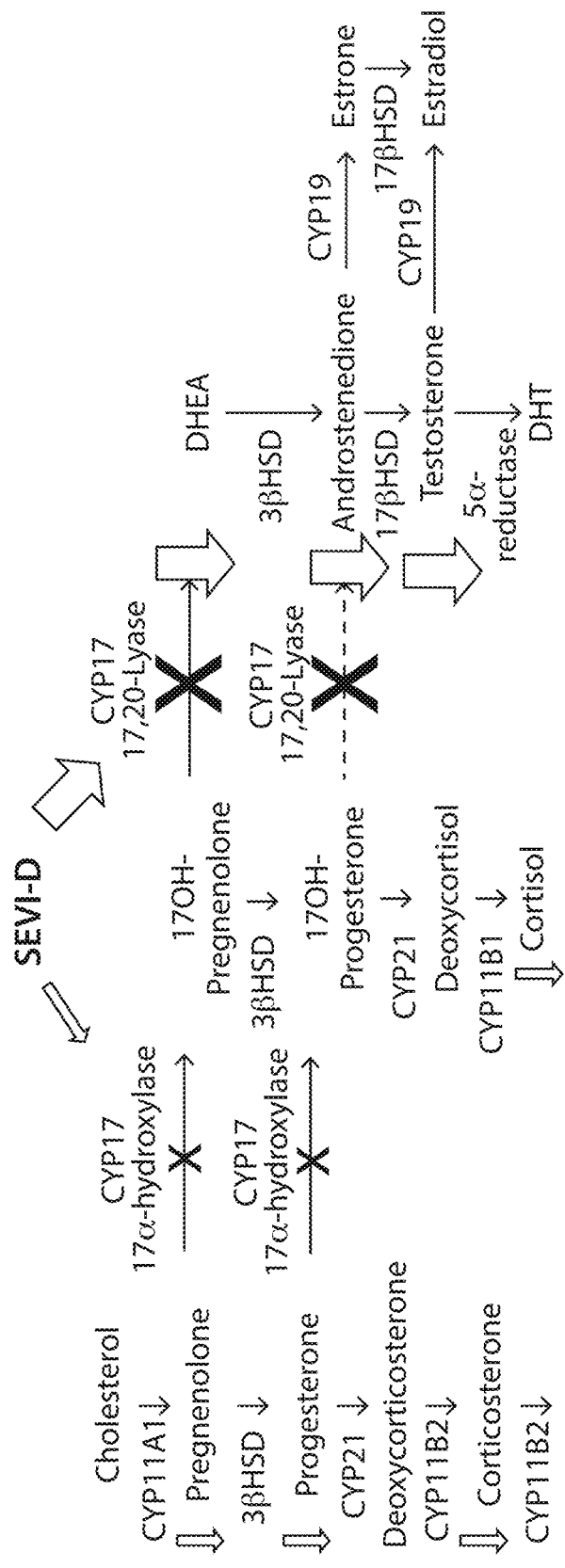
FIG. 8. depicts the endocrine profile for prostate cancer patients treated with SEVI-D.

FIG. 7 captures the endocrine profile for patients treated with SEVI, characterized by a modest ACTH increase, a modest cortisol decrease, a modest androgen decline, and a limited increase in "up-stream" steroids. FIG. 8 captures the endocrine profile for patients treated with SEVI-D, characterized by an ACTH and cortisol decrease, a decline in adrenal androgens, and "up-stream" steroids being unaffected or decreased, all relative to treatment with SEVI.

FIG. 9 summarizes the treatment emergent adverse events (TEAEs) for double failure patients: 1) treated with seviteronel and were not treated with dexamethasone at any time during the study (referred to as "NO Dex" in FIG. 9); 2) treated with seviteronel and ≥30 days of dexamethasone (referred to as "PLUS Dex" in FIG. 9); and 3) treated with seviteronel and dexamethasone within 3 days of Cycle 1 Day 1 study (referred to as "New subjects on Dex" in FIG. 9). FIG. 10 demonstrates the adverse event grade level breakdown for double failure patients: 1) treated with seviteronel and were not treated with dexamethasone at any time during the study (referred to as "NO Dex" in FIG. 10); and 2) treated with seviteronel and dexamethasone within 3 days of Cycle 1 Day 1 study (referred to as "New subjects on Dex" in FIG. 10).

FIG. 11 demonstrates the improved relative risk for patients treated with seviteronel and dexamethasone within 3 days of Cycle 1 Day 1 study (referred to as "New subjects on Dex" in FIG. 11) vs. patients treated with seviteronel and were not treated with dexamethasone at any time during the study (referred to as "NO Dex" in FIG. 11).

Treatment of Breast Cancer in Men and Women With SEVI and SEVI-D

Figure 13:
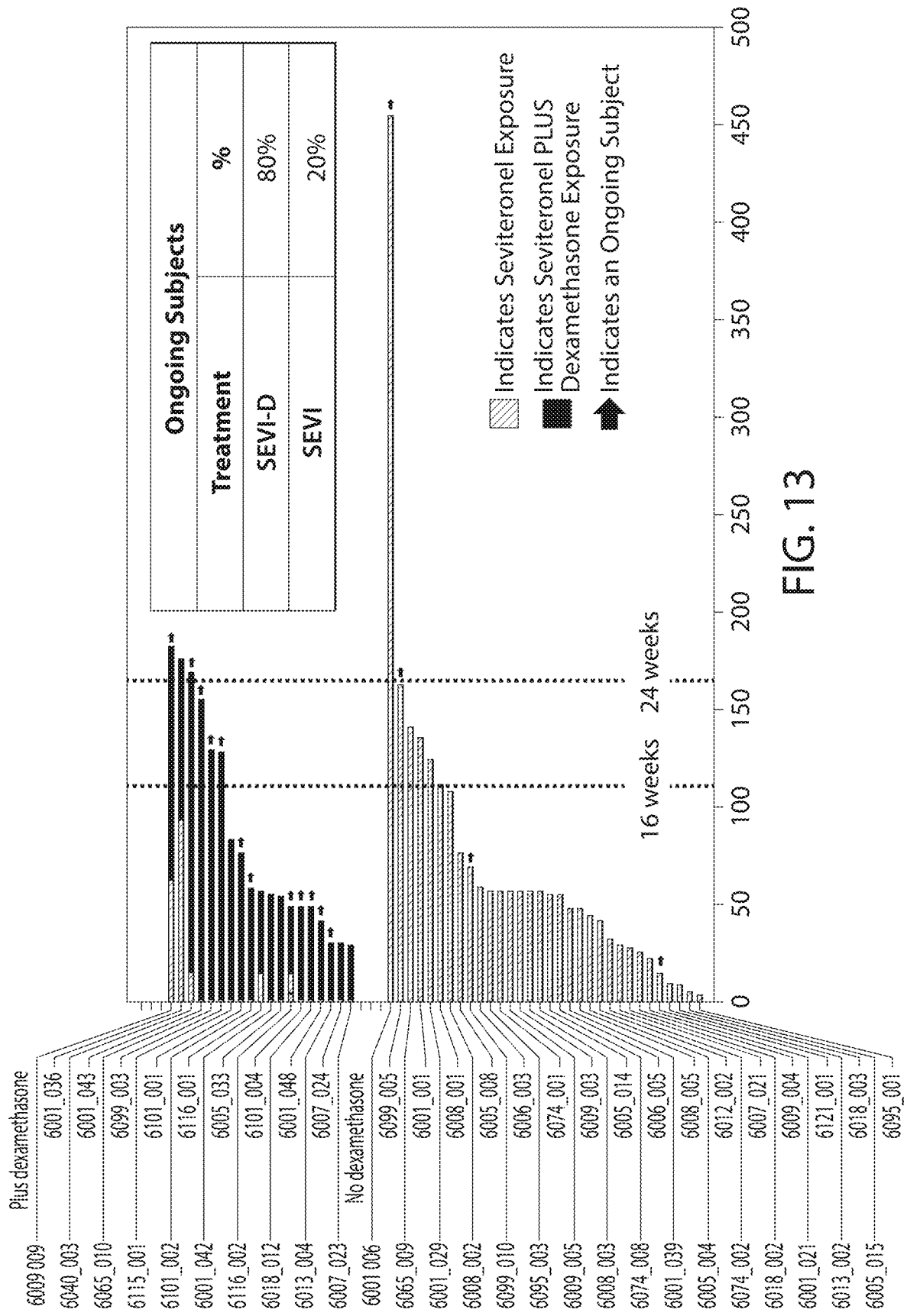
FIG. 13. depicts triple negative breast cancer study results as Swim Plots for patients treated with SEVI or SEVI-D.
Figure 14:
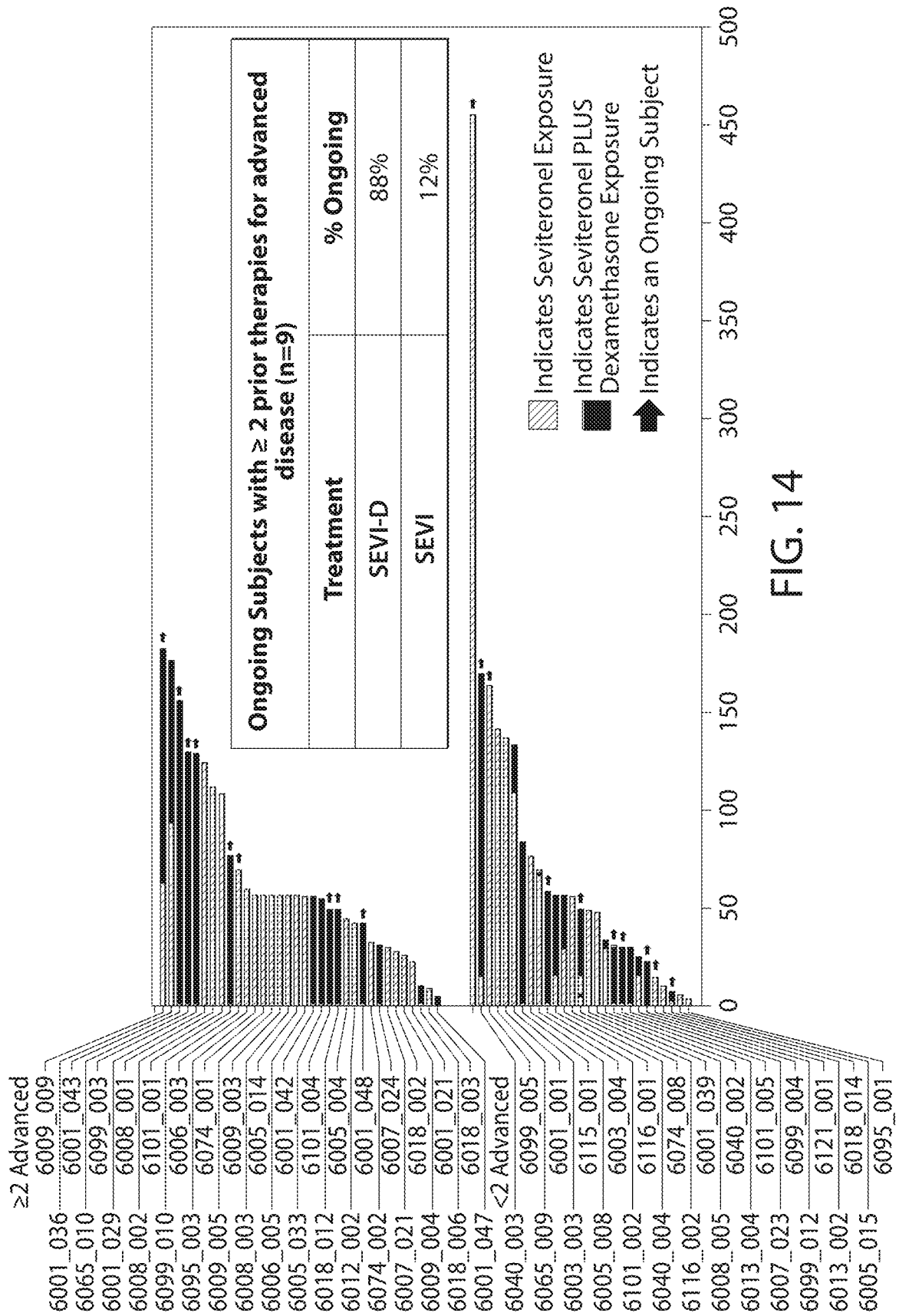
FIG. 14. depicts triple negative breast cancer study results as Swim Plots for patients treated with SEVI or SEVI-D and either having ≥2 prior therapies for advanced disease or <2 prior therapies for advanced disease.
Figure 15:
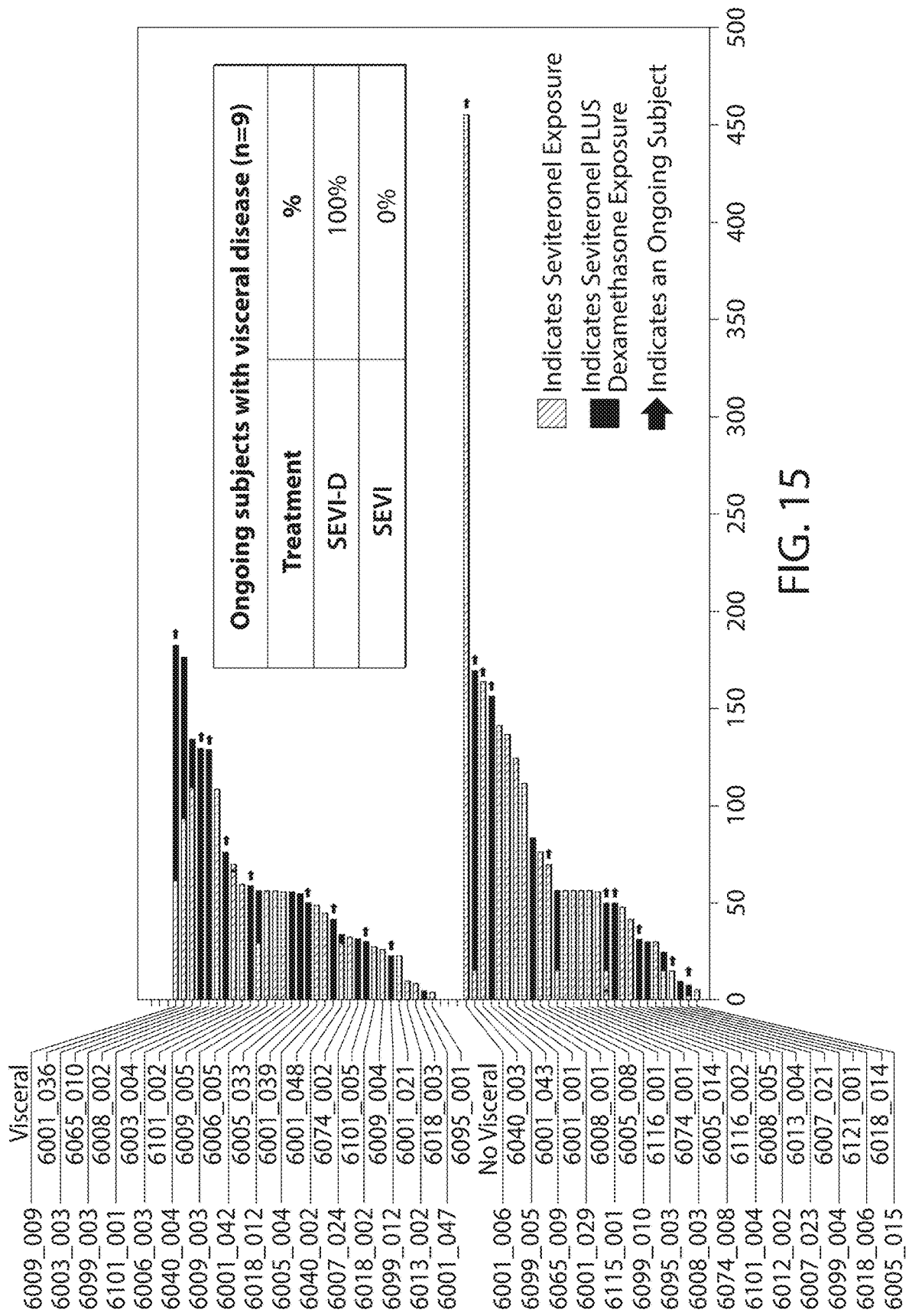
FIG. 15. depicts triple negative breast cancer study results as Swim Plots for patients treated with SEVI or SEVI-D and either having visceral disease or not having visceral disease.
Figure 16:
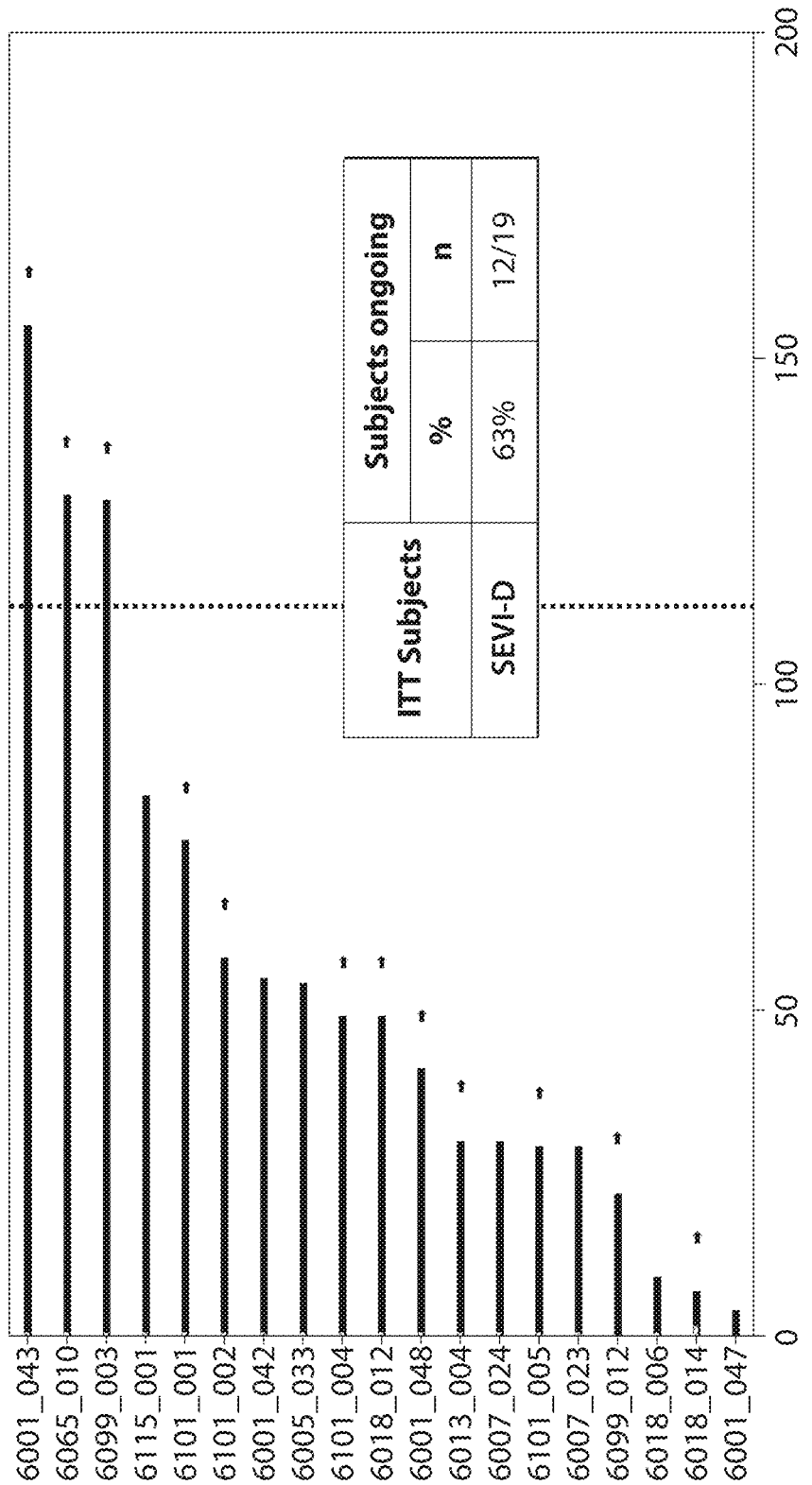
FIG. 16. depicts triple negative breast cancer study results for females treated with seviteronel and dexamethasone within 3 days of Cycle 1 Day 1 study (referred to as "New subjects on Dex" in FIG. 16).
Figure 17:
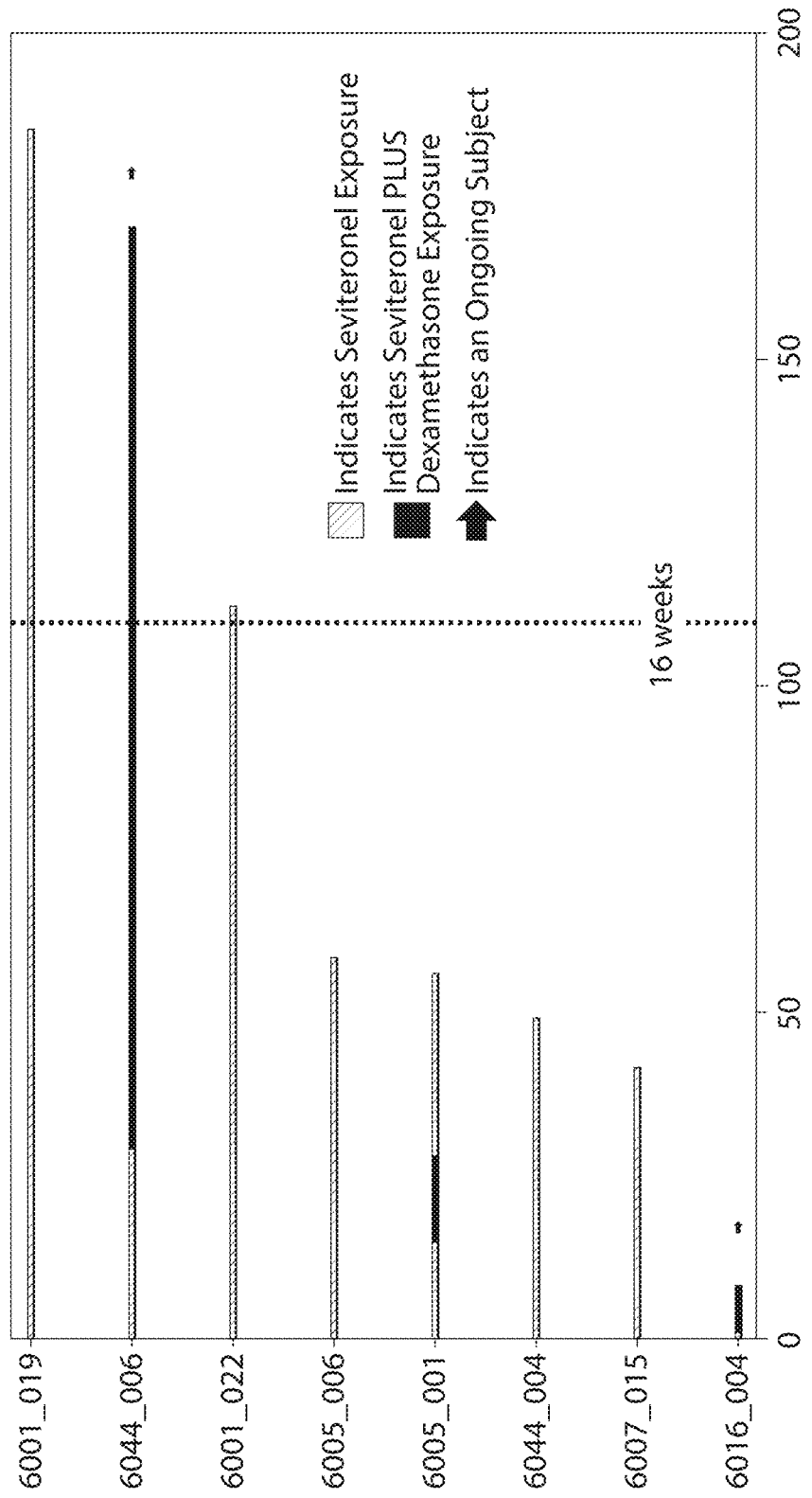
FIG. 17. depicts breast cancer study results for: 1) males treated with seviteronel and were not treated with dexamethasone at any time during the study; and 2) males treated with seviteronel and ≥30 days of dexamethasone.

FIG. 12 captures the breast cancer study results for: 1) patients treated with seviteronel and were not treated with dexamethasone at any time during the study (referred to as "NO Dex" in FIG. 12); 2) patients treated with seviteronel and ≥30 days of dexamethasone (referred to as "PLUS Dex" in FIG. 12); and 3) patients treated with seviteronel and dexamethasone within 3 days of Cycle 1 Day 1 study (referred to as "New subjects on Dex" in FIG. 12). FIG. 13 summarizes the triple negative breast cancer study results as Swim Plots for patients treated with SEVI or SEVI-D, with 83% of the SEVI-D patients meeting CBR16 criteria. FIG. 14 summarizes the triple negative breast cancer study results as Swim Plots for patients treated with SEVI or SEVI-D and either having ≥2 prior therapies for advanced disease or <2 prior therapies for advanced disease. FIG. 15 summarizes the triple negative breast cancer study results as Swim Plots for patients treated with SEVI or SEVI.D and either having visceral disease or not having visceral disease. FIG. 16 captures the triple negative breast cancer study results for females treated with seviteronel and dexamethasone within 3 days of Cycle 1 Day 1 study (referred to as "New subjects on Dex" in FIG. 16), with 63% of the subjects continuing with SEVI-D treatment. FIG. 17 captures the breast cancer study results for: 1) males treated with seviteronel and were not treated with dexamethasone at any time during the study; and 2) males treated with seviteronel and ≥30 days of dexamethasone.

Figure 18:
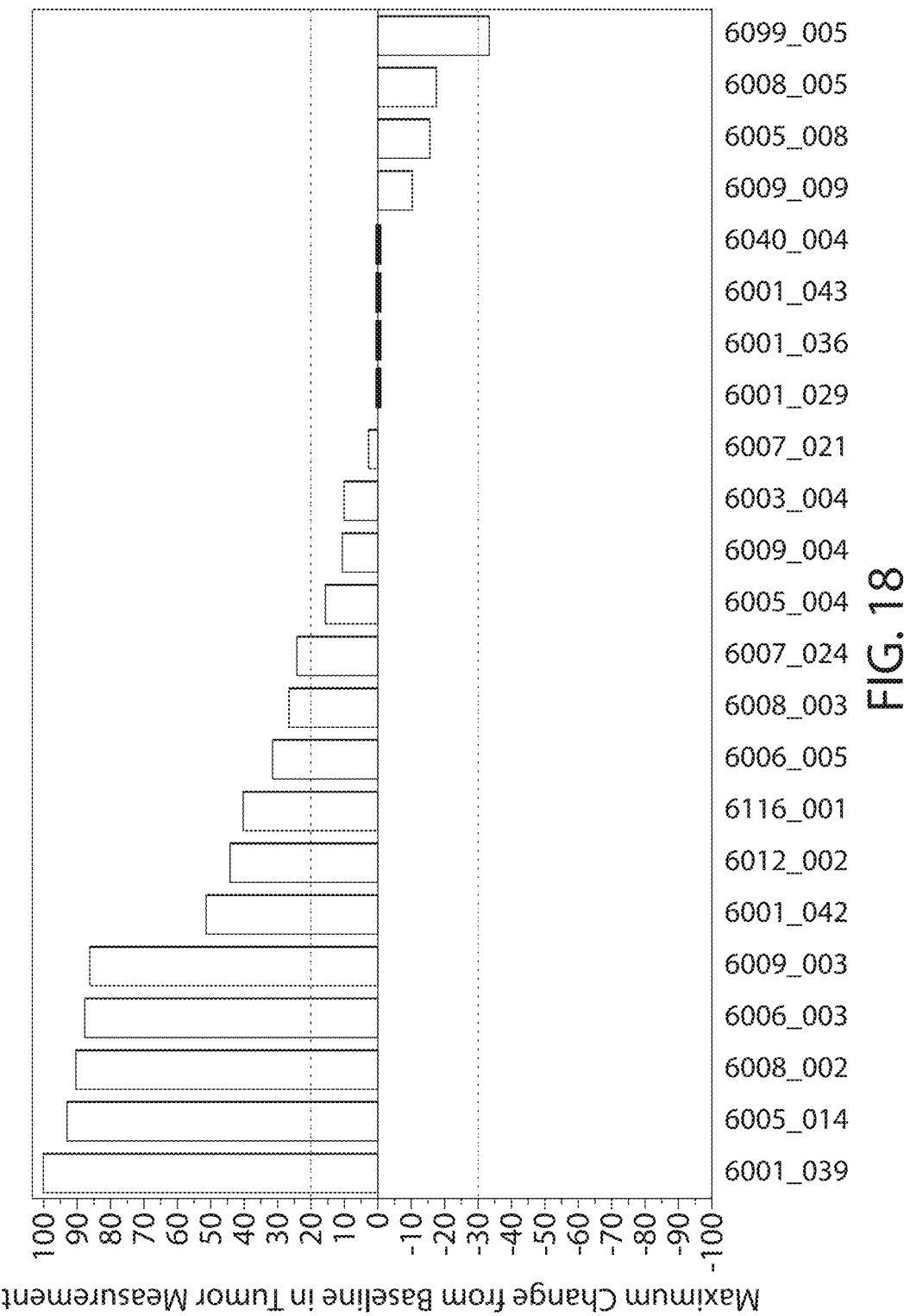
FIG. 18. depicts percent change of breast cancer tumor measurements as a waterfall plot for female patients treated with SEVI and. SEV-D.
Figure 19:
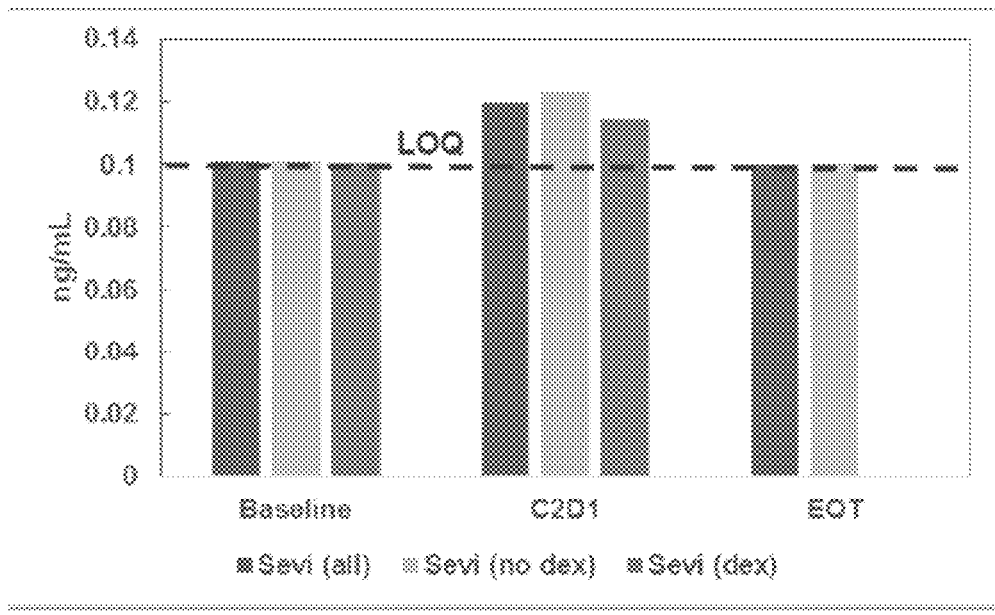
FIG. 19. depicts the response of progesterone in female breast cancer subjects: 1) treated with seviteronel and were not treated with dexamethasone at any time during the study (referred to as "Sevi (no dex)" in FIG. 19); and 2) treated with seviteronel and ≥30 days of dexamethasone (referred to as "Sevi (dex)" in FIG. 19).
Figure 20:
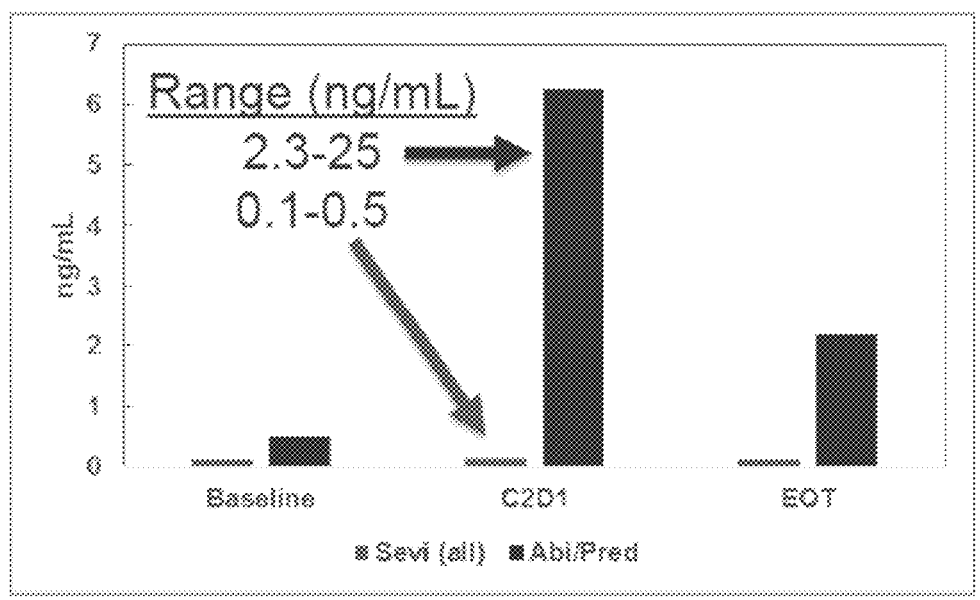
FIG. 20. depicts the lack of clinically relevant increases in progesterone in ER+ breast cancer patients treated with SEVI or SEVI-D vs. patients treated with abiraterone and prednisone (referred to as "Abi/Pred" in FIG. 20).

FIG. 18 illustrates the percent change of breast cancer tumor measurements as a waterfall plot for female patients treated with SEVI and SEV-D. FIG. 19 captures the response of progesterone in female breast cancer subjects: 1) treated with seviteronel and were not treated with dexamethasone at any time during the study (referred to as "Sevi (no dex)" in FIG. 19); and 2) treated with seviteronel and ≥30 days of dexamethasone (referred to as "Sevi (dex)" in FIG. 19). FIG. 20 demonstrates the lack of clinically relevant increase in progesterone in ER$^+$ breast cancer patients treated with SEVI or SEVI-D vs. patients treated with abiraterone and predisone (referred to as "Abi/Pred" in FIG. 20).

FIG. 21 summarizes the treatment emergent adverse events (TEAEs) for female breast cancer patients: 1) treated with seviteronel and were not treated with dexamethasone at any time during the study (referred to as "NO Dex" in FIG. 21); 2) treated with seviteronel and ≥30 days of dexamethasone (referred to as "PLUS Dex" in FIG. 21); and 3) treated with seviteronel and dexamethasone within 3 days of Cycle 1 Day 1 study (referred to as "New subjects on Dex" in FIG. 21). FIG. 22 demonstrates the adverse event grade level breakdown for female breast cancer patients: 1) treated with seviteronel and were not treated with dexamethasone at any time during the study (referred to as "NO Dex" in FIG. 22); and 2) treated with seviteronel and dexamethasone within 3 days of Cycle 1 Day 1 study (referred to as "New subjects on Dex" in FIG. 22). FIG. 23 demonstrates the improved relative risk for breast cancer patients treated with seviteronel and dexamethasone within 3 days of Cycle 1 Day 1 study (referred to as "NEW Dex" in FIG. 23) vs. patients treated with seviteronel and were not treated with dexamethasone at any time during the study (referred to as "NO Dex" in FIG. 23).

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A pharmaceutical composition comprising: a) seviteronel, or salt thereof; b) dexamethasone, or salt thereof; and c) a pharmaceutically acceptable carrier.

2. The composition of claim 1, wherein the amount of seviteronel in the composition is in a range of about 150 mg-750 mg.

3. The composition of claim 1, wherein the amount of dexamethasone in the composition is in a range of about 0.25 mg-1000 mg.

4. The composition of claim 1, wherein the amount of seviteronel in the composition is in a range of about 150 mg-750 mg, and the amount of dexamethasone in the composition is in a range of about 0.25 mg-1000 mg.

5. The composition of claim 1, wherein the amount of seviteronel in the composition is in a range of about 400 mg-650 mg, and the amount of dexamethasone in the composition is in a range of about 0.40 mg-0.60 mg.

6. The composition of claim 1, wherein the amount of seviteronel in the composition is 600 mg, and the amount of dexamethasone in the composition is 0.5 mg.

7. The composition of claim 1, wherein the amount of seviteronel in the composition is 450 mg, and the amount of dexamethasone in the composition is 0.5 mg.

8. A dosing regimen for the treatment of prostate cancer or breast cancer, the dosing regimen comprising seviteronel, or salt thereof; and dexamethasone, or salt thereof.

9. The dosing regimen of claim 8, wherein the amount of seviteronel is in a range of about 150 mg-750 mg.

10. The dosing regimen of claim 8, wherein the amount of dexamethasone is in a range of about 0.25 mg-1000 mg.

11. The dosing regimen of claim 8, wherein the amount of seviteronel in is in a range of about 150 mg-750 mg, and the amount of dexamethasone is in a range of about 0.25 mg-1000 mg.

12. The dosing regimen of claim 8, wherein the amount of seviteronel is in a range of about 400 mg-650 mg, and the amount of dexamethasone is in a range of about 0.40 mg-0.60 mg.

13. The dosing regimen of claim 8, wherein the amount of seviteronel is 600 mg, and the amount of dexamethasone is 0.5 mg.

14. The dosing regimen of claim 8, wherein the amount of seviteronel is 450 mg, and the amount of dexamethasone is 0.5 mg.

15. The dosing regimen of claim 8, wherein seviteronel and dexamethasone are administered concurrently.

16. The dosing regimen of claim 8, wherein seviteronel and dexamethasone are administered sequentially.

17. A method of ameliorating, mitigating, and/or managing breast cancer or prostate cancer in a subject, comprising administering to the subject in need thereof a pharmaceutical composition of claim 1.

18. A method of ameliorating, mitigating, and/or managing breast cancer or prostate cancer in a subject having breast cancer or prostate cancer, comprising administering to said subject a pharmaceutical composition of claim 1.

19. A method of ameliorating, mitigating, and/or managing breast cancer or prostate cancer in a subject, comprising administering to the subject in need thereof a dosing regimen comprising seviteronel, or salt thereof; and dexamethasone, or salt thereof.

20. A method of ameliorating, mitigating, and/or managing breast cancer or prostate cancer in a subject having breast cancer or prostate cancer, comprising administering to said subject a dosing regimen of claim 8.

21. The method of claim 19, wherein the amount of seviteronel in is in a range of about 150 mg-750 mg, and the amount of dexamethasone is in a range of about 0.25 mg-1000 mg.

22. The method of claim 19, wherein the amount of seviteronel is in a range of about 400 mg-650 mg, and the amount of dexamethasone is in a range of about 0.40 mg-0.60 mg.

23. The method of claim 19, wherein seviteronel and dexamethasone are administered concurrently.

24. The method of claim 19, wherein seviteronel and dexamethasone are administered sequentially.

\* \* \* \* \*